(12) United States Patent
Gitlin et al.

(10) Patent No.: US 11,864,798 B2
(45) Date of Patent: Jan. 9, 2024

(54) Y-FRAME EXTERNAL BONE FIXATOR

(71) Applicant: ATLAS TECHNOLOGIES, LLC, Hewlett, NY (US)

(72) Inventors: David Gitlin, Woodmere, NY (US); Lev Gitlin, Forest Hills, NY (US)

(73) Assignee: Gitlin LLC, Naples, FL (US)

( * ) Notice: Subject to any disclaimer, the term of this patent is extended or adjusted under 35 U.S.C. 154(b) by 818 days.

(21) Appl. No.: 16/588,477

(22) Filed: Sep. 30, 2019

(65) Prior Publication Data

US 2021/0093359 A1    Apr. 1, 2021

(51) Int. Cl.
*A61B 17/64* (2006.01)
*A61B 17/66* (2006.01)

(52) U.S. Cl.
CPC ........ *A61B 17/645* (2013.01); *A61B 17/6416* (2013.01); *A61B 17/6425* (2013.01); *A61B 17/6458* (2013.01); *A61B 17/6491* (2013.01); *A61B 17/66* (2013.01)

(58) Field of Classification Search
CPC .............. A61B 17/645; A61B 17/6416; A61B 17/6425; A61B 17/6458; A61B 17/6491; A61B 17/66
USPC ..................................... 606/54, 59, 286, 287
See application file for complete search history.

(56) References Cited

U.S. PATENT DOCUMENTS 3,651,803 A  *  3/1972  Bimler ............... A61B 17/6408
                                                        602/16
2004/0260223 A1  12/2004  Roukis et al.
2006/0195089 A1  *  8/2006  LeHuec ............. A61B 17/7059
                                                        606/280
2006/0235383 A1  10/2006  Hollawell
2006/0247629 A1  *  11/2006  Maughan ........... A61B 17/6466
                                                        606/53
2007/0123856 A1  5/2007  Deffenbaugh et al.
2009/0299369 A1  *  12/2009  Orbay .................... A61B 17/80
                                                        606/70
2010/0249779 A1  9/2010  Hotchkiss et al.
2010/0298827 A1  *  11/2010  Cremer ............. A61B 17/6466
                                                        606/54

(Continued)

FOREIGN PATENT DOCUMENTS

WO    WO-9716128 A1  *  5/1997  ......... A61B 17/6425

OTHER PUBLICATIONS

DePuy Synthes Trauma, "DePuySynthes Trauma External Fixator Systems MR-Conditional Labeling Update", Jul. 2004, pp. 1-3.

(Continued)

*Primary Examiner* — Eduardo C Robert
*Assistant Examiner* — David C Comstock
(74) *Attorney, Agent, or Firm* — Ronald D. Slusky

(57) ABSTRACT

In an embodiment of the invention, a fixator for fixating bone fractures includes a Y-frame having superior, anterior and posterior arms. The arms may be slotted and may accept mounting hardware for supporting fixation pins or transfixion pins. Various components of mounting hardware may be able to be adjusted either in discrete steps or in continuous manner, for various degrees of either translation or rotation. The Y-frame may be rigid, or may have joints that allow either angulation or arm-twisting adjustment. Arms may be provided joinable interchangeably to a hub. A kit of such parts may be provided.

22 Claims, 20 Drawing Sheets

(56) References Cited

U.S. PATENT DOCUMENTS

| | | | |
|---|---|---|---|
| 2010/0331840 A1* | 12/2010 | Ross | A61B 17/62 606/54 |
| 2012/0203225 A1 | 8/2012 | Mingozzi et al. | |
| 2012/0209264 A1* | 8/2012 | Zandona | A61B 17/6466 606/54 |
| 2012/0209266 A1 | 8/2012 | Ottoboni et al. | |
| 2012/0303032 A1 | 11/2012 | Mirza et al. | |
| 2013/0110110 A1 | 5/2013 | Waisman | |
| 2013/0253514 A1 | 9/2013 | Starr | |
| 2016/0038184 A1 | 2/2016 | Erickson | |
| 2018/0008315 A1* | 1/2018 | Currier | A61B 17/6408 |
| 2019/0119064 A1* | 4/2019 | Wong | A61B 17/8869 |

OTHER PUBLICATIONS

Jonathan Cluett, "External Fixation-Fractures and Broken Bones", Mar. 2016, pp. 1-2, orthopedics.about.com/cs/brokenbones/g/exfix.htm.

Orthofix Orthopedics, "Minirail Fixator System Operative Technique Foot Applications", Oct. 2009, pp. 1-8.

Makhdoom et al., "Open Proximal & Distal Fractures of Tibia Treated with Naseer Awais External Fixator with T-Clamp", Journal of Pakistan Medical Association, Mar. 2016, pp. 1-12, jpma.org.pk/article-details/7401?article_id=7401.

Wright Medical Technology, Inc., "RX-Fix Mini Rail External Fixator", Dec. 2014, pp. 1-12.

Orthofix, "Ankle External Fixation System Adult Calcaneal Minifixator" 2009 pp. 1-15, web.orthofix.com/Products/Pages/Calcaneal-Minifixator.aspx?catid=21.

Taimin, "Surgical Products Implants", 2001, pp. 1-2, www.taimin.com.br/equipamentos-medicos/trauma#fixadores-externos.

Medical Expo, "Orthopedic Surgery External Fixation Systems, Orthopedic Connectors", 2009, pp. 1-15, www.medicalexpo.com/medical-manufacturer/external-fixation-system-4052.html.

Baumer, "Orthopedic External Fixation" 2001, pp. 1-10, www.baumer.com.br/baumer/site/produto/index.php?acao=listar&cat=157&catAtivo=84&idioma=Ingles.

* cited by examiner

Y-FRAME EXTERNAL BONE FIXATOR

FIELD OF THE INVENTION

The invention pertains to bone fixation. More specifically, the invention relates to external frames and hardware used for the stabilization of bones in a variety of medical situations.

BACKGROUND OF THE INVENTION

The terminology and descriptions contained herein are principally within the art field of, and for those skilled in the art of, orthopedic medicine. As such, only brief explanations of known subject matter within this art field will be provided because the details will be well known to those skilled in this art. The present invention, however, will be thoroughly described.

External bone fixation incorporates the use of certain structures and instruments to assist in bone surgery as an alternative or an adjunct to internal fixation. External fixation is also used in situations that prohibit the use of internal fixation such as infection and open wounds, as well as in cases of severe deformity where acute deformity correction is not possible. In the lower extremity, for example, an external fixation construct can be used for fusion surgery as well as any stabilization or distraction procedure, and fracture repair.

One well known external fixator is called the Ilizarov frame, comprised of one or more round rings. This, and other types of similar external systems, have been in use for many years. They rely on wires and pins placed into the bones of a patient, that are then attached to the rings or other structures outside of the patient's body. The rings or other structures are then interconnected to form an overall external fixation construct.

In the foot, for example, smaller external fixators are more desirable because they are better able to fixate the smaller bones of the foot than a large and bulky Ilizarov-type ring fixator. And overall, attempts over the years to create a simple to use, and simple to teach to medical professionals, external fixation system that can be used for extremity surgery in general, and foot surgery in particular, are not believed to have yielded optimal results. Thus, it continues to be desirable to improve certain design features of external fixation for improved surgeon usability and improved patient outcomes.

SUMMARY OF THE INVENTION

In an embodiment of the invention, an apparatus for fixating a bone includes a Y-frame having a superior arm, an anterior arm and a posterior arm rigidly joined to each other at a central junction. The superior arm has a superior arm axis generally along a lengthwise direction of the superior arm, and a superior arm slot therethrough that extends generally along a portion of a length of the superior arm, defining a superior arm slot plane. The anterior arm has an anterior arm axis generally along a lengthwise direction of the anterior arm, and an anterior arm slot therethrough that extends generally along a portion of a length of the anterior arm, defining an anterior arm slot plane. The posterior arm has a posterior arm axis generally along a lengthwise direction of the posterior arm, and a posterior arm slot therethrough that extends generally along a portion of a length of the posterior arm, defining a posterior arm slot plane. The superior arm axis, anterior arm axis and posterior arm axis intersect at a common intersection point and occupy a common plane. None of the superior arm axis, the anterior arm axis and the posterior arm axis are collinear with each other. The apparatus also includes mounting hardware mountable on the arms through their respective slots. The mounting hardware is able to occupy a plurality of translational positions along the slots, and is suitable for holding pins that fixate the bone.

In various embodiments, the apparatus further comprises a superior arm side hole or a superior arm end hole or an anterior arm side hole or an anterior arm end hole or a posterior arm side hole or a posterior arm end hole.

In an embodiment, the apparatus further comprises a central axis hole perpendicular to the common plane, and passes through the common intersection point of the arms.

In an embodiment, the Y-frame comprises a radiolucent material and comprises, in the radiolucent material, markers in desired locations, the markers being made of a radiopaque material.

In an embodiment, the mounting hardware comprises a clamp having a clamp cross-hole having internal grooves having a clamp hole angular spacing of the internal grooves, and comprises a rocker nut having an external tooth engageable with the clamp cross-hole having internal grooves.

In an embodiment, the mounting hardware comprises a pin-holding assembly that provides adjustability in at least five total degrees of freedom of translation and rotation, and comprises a clamping bolt that provides adjustability in fewer than five total degrees of freedom of translation and rotation.

In various embodiments at least one of the arms comprises repeated features, the mounting hardware comprises shim washers, and at least one of the shim washers has a complementary underside feature that is complementary with the repeated feature. In an embodiment, the repeated features in the arm are grooves are generally parallel to each other, and the complementary underside feature comprises complementary grooves. In an embodiment, the repeated features are countersinks in the arm and the complementary underside feature comprises a protrusion that is conical or partially conical. In at least some rotational orientations of the shim washer relative to the arm, the complementary feature can engage with the repeated features, and, in at least some other rotational orientations of the shim washer relative to the arm, the complementary feature can avoid engaging with the repeated feature. In an embodiment, the mounting hardware comprises a yoke that includes a complementary underside feature on an underside of the yoke that is complementary with the repeated feature. In an embodiment, the mounting hardware comprises a pin-holding apparatus comprising a yoke having an internal taper and comprises a clamp having an external taper complementary to the internal taper, where the clamp is disposed to grip a pin upon action of the internal taper against said external taper. In an embodiment, the external taper on the clamp is a segment of a conical surface, and the internal taper inside the yoke is a segment of a conical surface.

In an embodiment of the invention, the mounting hardware comprises shim washers, and the shim washers have nesting features suitable to nest with other shim washers when stacked. In an embodiment, the mounting hardware further comprises a yoke, and the yoke has a nesting feature suitable to nest with one of the shim washers.

In another embodiment of the invention, an apparatus for fixating a bone includes a Y-frame comprising a superior arm, an anterior arm and a posterior arm, the arms having respective arm axes generally along respective lengthwise directions of the arms, The superior arm, anterior arm and posterior arm are individual components that are separately attachable to a hub. The apparatus also includes mounting hardware that is mountable on the arms and suitable for holding pins that fixate the bone. In an embodiment, the hub comprises, on its external surface, planar surfaces and at least some of the arms comprise, on a respective hub-facing surface, shapes that are complementary to the hub and are capable of interacting with the hub grooves to constrain a configuration of the arms relative to the hub. In an embodiment, the hub comprises, on its external surface, a surface that is not smooth, and at least one of the arms comprises, on its hub-facing surface, a surface that is complementary to the hub surface, and at least another one of the arms comprises, on its hub-facing surface, a smooth surface that does not engage with the hub-facing surface. In an embodiment, the hub comprises, on its external surface, hub grooves, and at least some of the arms comprise, on a respective hub-facing surface, hub-facing grooves that are complementary to the hub grooves and are capable of interacting with the hub grooves to constrain a configuration of the arms relative to the hub. In an embodiment, the hub grooves comprise a first set of grooves parallel to each other. In an embodiment, the hub grooves further comprise a second set of grooves parallel to each other and generally perpendicular to grooves in the first set of grooves. In an embodiment, the apparatus further comprises attachment means for attaching the arms to the hub.

In another embodiment of the invention, an apparatus for fixating a bone includes a first Y-frame that comprises a superior arm, an anterior arm and a posterior arm, the arms having respective arm axes generally along respective lengthwise direction of the arms. None of these axes are collinear with each other, and the axes intersect at a common intersection point and occupy a common first Y-frame plane. The apparatus further includes a second Y-frame, that comprises a superior arm, an anterior arm and a posterior arm, the arms having respective arm axes generally along respective lengthwise direction of the arms. None of these axes are collinear with each other, and the axes intersect at a common intersection point and occupy a common second Y-frame plane. In addition, the apparatus includes a transfixion pin anchored at or near a first end to the first Y-frame and anchored at or near a second end to the second Y-frame. The first Y-frame plane and the second Y-frame plane are constrained through the transfixion pin to be parallel to each other. In an embodiment, the first Y-frame has a flat surface on one of its arms, the second Y-frame has a flat surface on one of its arms, and the transfixion pin is anchored in direct contact with each of these flat surfaces. In an embodiment, each arm has a slot and a clamping bolt disposable within the slot that maintains the first Y-frame and second Y-frame parallel to each other by the constraint through the transfixion pin. In an embodiment, each arm has a slot and a clamping bolt disposable within the slot such that the clamping bolt is prevented from rotating about its own lengthwise axis within the slot. In an embodiment, the first Y-frame and second Y-frame are identical to each other. In an embodiment, the apparatus further comprises a pin-holding apparatus suitable for holding a fixation pin for fixating the bone.

In another embodiment of the invention, an apparatus for fixating a bone includes a first Y-frame that comprises a superior arm, an anterior arm and a posterior arm, the arms having respective arm axes generally along respective lengthwise direction of the arms, None of these axes are collinear with each other, and the axes intersect at a common intersection point and occupy a common first Y-frame plane. The apparatus further includes a second Y-frame comprising a superior arm, an anterior arm and a posterior arm, the arms having respective arm axes generally along respective lengthwise direction of the arms. None of these axes are collinear with each other, and the axes intersect at a common intersection point and occupy a common second Y-frame plane. In addition, the apparatus includes a transfixion pin anchored at or near a first end to the first Y-frame and anchored at or near a second end to the second Y-frame. The first Y-frame plane and the second Y-frame plane are constrained through the transfixion pin to a defined relative orientation to each other with respect to a rotational axis that is a longitudinal direction of the transfixion pin. In an embodiment, the apparatus comprises a transfixion pin extending between the first Y-frame and second Y-frame, and the transfixion pin is grasped at or near each of its ends by a respective clamping bolt. In an embodiment, the transfixion pin has a first flat region in a first clamped portion of the transfixion pin and a second flat region in a second clamped portion of the transfixion pin, the first flat region and second flat region being parallel to each other. In an embodiment, the transfixion pin has a first flat region in a first clamped portion of the transfixion pin and a second flat region in a second clamped portion of the transfixion pin, the first flat region and second flat region being coplanar with each other. In an embodiment, the transfixion pin has a first flat region in a first clamped portion of the transfixion pin and a second flat region in a second clamped portion of the transfixion pin, the first flat region and second flat region lying in a plane that is parallel to a long axis of the pin. In an embodiment, the transfixion pin has a first flat region in a first clamped portion of the transfixion pin and a second flat region in a second clamped portion of the transfixion pin, wherein the first flat region of the transfixion pin is grasped in a first clamping bolt and the second flat region of the transfixion pin is grasped by a second clamping bolt. In an embodiment, the apparatus further comprises a pin-holding apparatus suitable for holding a fixation pin for fixating the bone.

In another embodiment of the invention, a kit for fixation of bone includes a Y-frame comprising a superior arm, an anterior arm, and a posterior arm, the arms having respective slots therein; a clamping bolt; a pin-holding assembly comprising a rocker nut or pin-holding assembly that discretizes an angular position and comprises a rocker nut or pin-holding assembly that permits continuous adjustment, and shim washers that can optionally be used in said pin-holding assembly. In an embodiment, some of the shim washers permit or can be used to permit continuous adjustment of a translational position, and the shim washers in a different orientation, or other shim washers, can be used to permit discrete adjustment of the translational position.

In another embodiment of the invention, a kit for fixation of bone includes a superior arm, an anterior arm, a posterior arm, and a hub, wherein the superior arm, anterior arm and posterior arm are joinable to the hub.

BRIEF DESCRIPTION OF THE ILLUSTRATIONS

The patent or application file contains at least one drawing executed in color. Copies of this patent or patent application publication with color drawing(s) will be provided by the Office upon request and payment of the necessary fee.

Embodiments of the invention are further described but are in no way limited by the following illustrations:

DETAILED DESCRIPTION OF THE INVENTION

Directional and spatial anatomical terminology that may be used herein is well known to those skilled in the art. For instance, the term "medial" typically means closer to the midline of the body, and "lateral" typically means farther from the midline of the body. Further terms, such as "proximal", "distal", "anterior", "posterior", "superior", "inferior", and other such terms shall have their common and ordinary meanings in the art.

Basic Y-Frame

Figure 1:
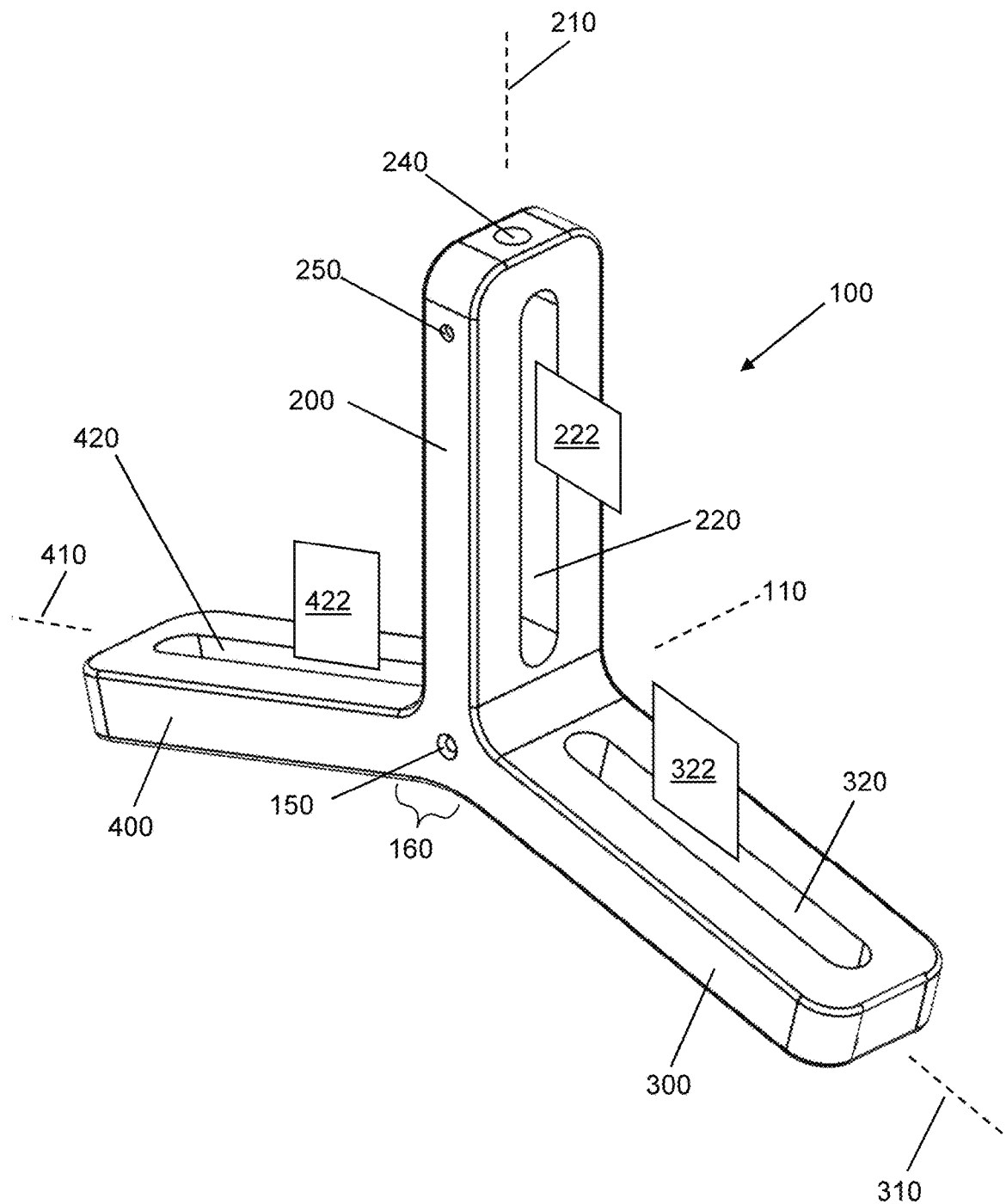
FIG. 1 is a top perspective view of a Y-frame of an embodiment of the invention.
Figure 3:
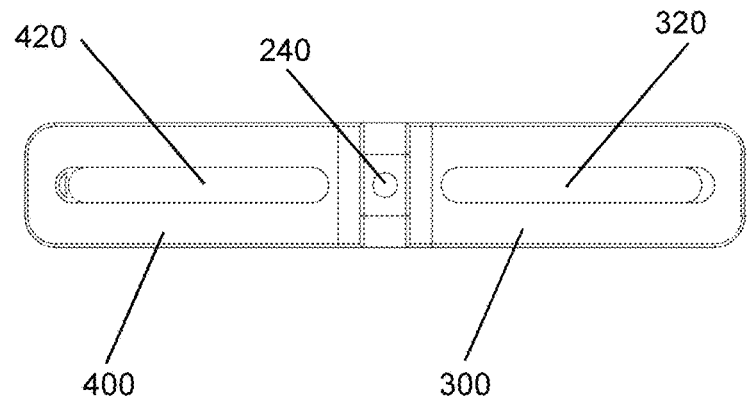
FIG. 3 is a top view of the Y-frame of FIG. 1.

Referring now to FIGS. 1-6, an embodiment of the invention comprises a Y-frame 100. FIG. 1 is a perspective view. FIGS. 2-6 are, respectively, views from the side, top, anterior, posterior and bottom. In the embodiment that is shown in FIG. 1, the Y-frame 100 is substantially rigid and the Y-frame 100 itself is non-adjustable. As illustrated, Y-frame 100 may have an axis 110 and an axis hole 150 as discussed herein. In an embodiment, the Y-frame has three arms, designated as a superior arm 200, an anterior arm 300, and a posterior arm 400. In various embodiments, these arms are identical to each other, or the arms differ in length or other dimensions or other features.

In an embodiment, superior arm 200 has superior arm axis 210 generally along its lengthwise direction. In an embodiment, superior arm 200 has therethrough a superior arm slot 220, extending generally along a portion of the length of superior arm 200, and generally parallel to superior arm axis 210. In an embodiment, superior arm slot 220 has a superior arm slot plane 222 extending through the middle of superior arm slot 220. In an embodiment, superior arm 200 has a superior arm end hole 240, whose axis aligns with superior arm axis 210. In an embodiment, superior arm 200 has a superior arm side hole 250, whose axis is perpendicular to superior arm axis 210. Superior arm side hole 250 is illustrated as intersecting with superior arm slot 220. However, in an alternate embodiment, the superior arm side hole 250 extends through the solid uppermost portion of superior arm 200 and does not intersect with superior arm slot 220. In various embodiments, similar side holes and end holes are formed in the other arms 300, 400.

In an embodiment, anterior arm 300 has anterior arm axis 310 generally along its lengthwise direction. In an embodiment, anterior arm 300 has therethrough an anterior arm slot 320, extending generally along a portion of the length of anterior arm 300. In an embodiment, anterior arm slot 320 has an anterior arm slot plane 322 extending through the middle of anterior arm slot 320.

In an embodiment, posterior arm 400 has a posterior arm axis 410 generally along its lengthwise direction. In an embodiment, posterior arm 400 has therethrough a posterior arm slot 420, extending generally along a portion of the length of posterior arm 400. In an embodiment, posterior arm slot 420 has a posterior arm slot plane 422 extending through the middle of posterior arm slot 420. Posterior arm 400 is shown as having a posterior arm end hole 440.

In an embodiment, the arms 200, 300, 400 are rigidly joined to each other at a central region 160. In various embodiments, superior arm slot plane 222, anterior arm slot plane 322 and posterior arm slot plane 422 are coplanar with each other, or are parallel with each other, even if not coplanar. In an embodiment, axes 210, 310, 410 intersect with each other at a common point in the central region of Y-frame 100. As illustrated in FIG. 1, all three of these axes 210, 310, 410 lie in a common plane. In an embodiment, the respective angles between axes 210, 310, 410 are chosen as a function of the intended use regarding anatomical features such as skeletal features. Superior arm 200, anterior arm 300 and posterior arm 400 can have any desired dimensions as appropriate to the need. In various embodiments, the dimensions of arms 200, 300, 400 are identical to each other, or the dimensions are different from each other, if desired.

In an embodiment, slots 220, 320, 420 extend through surfaces of respective arms 200, 300, 400 that generally face another one of respective arms 200, 300, 400. In various embodiments, slots 220, 320, 420 are of generally constant width (except near their ends), and are suitable to receive mounting hardware, as described elsewhere herein. In various embodiments, slots 220, 320, 420 are identical to each other, or are different from each other, if desired.

Figures 2, 4, 5:
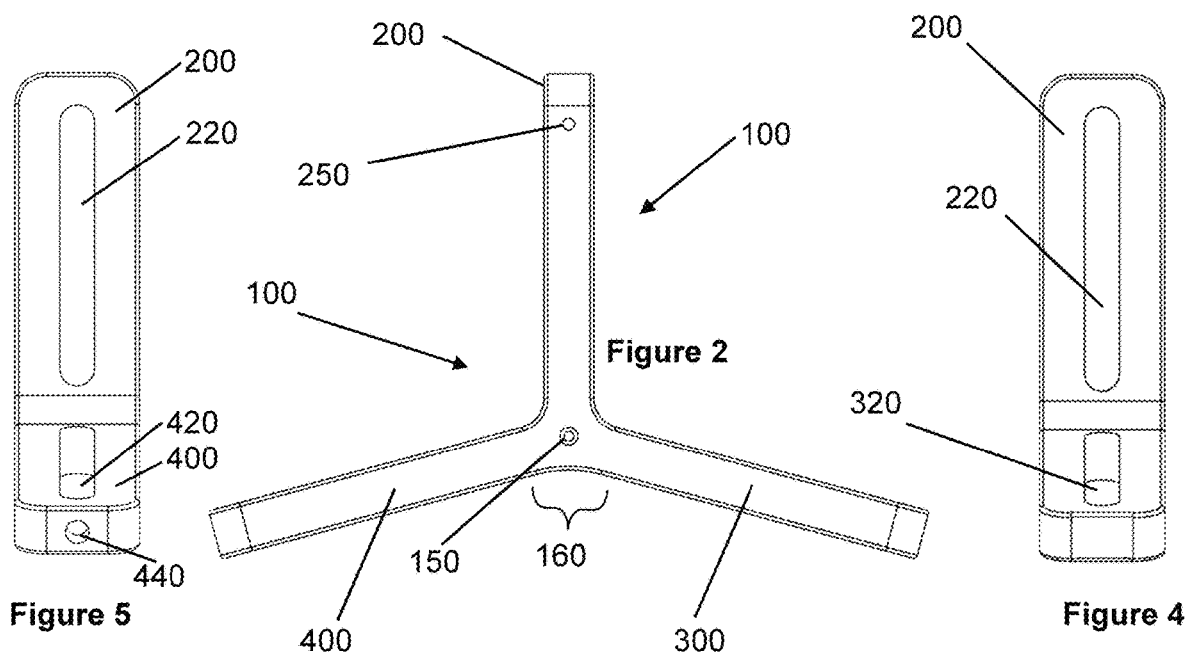
FIG. 2 is a side view of the Y-frame of FIG. 1.
FIG. 4 is an anterior view of the Y-frame of FIG. 1.
FIG. 5 is a posterior view of the Y-frame of FIG. 1.
Figure 6:
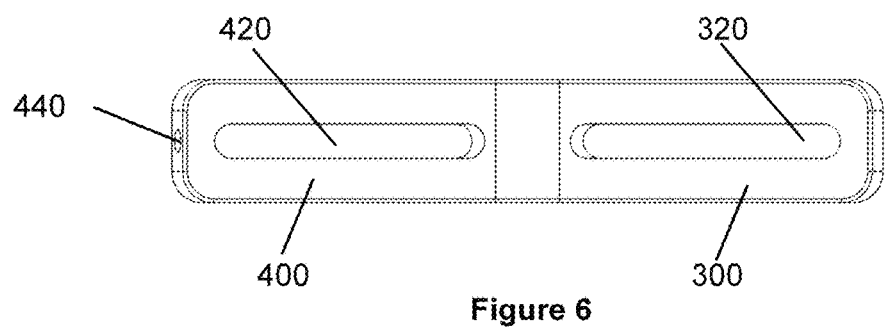
FIG. 6 is a bottom view of the Y-frame of FIG. 1.

Also illustrated is a central axis hole 150, formed through central region 160 (see FIGS. 1 and 2). In an embodiment, the central axis hole 150 coincides with Y-frame axis 110 and passes through the intersection point of superior arm axis 210, anterior arm axis 310 and posterior arm axis 410.

In various embodiments, anterior arm 300 and posterior arm 400 include any variety of arm end holes and arm side holes similar to superior arm end hole 240, and superior arm side hole 250, whether or not these are illustrated. In an embodiment, any such holes are useful for alignment of various hardware, or for temporarily holding pins or other components, or for other purposes as may be desired by a health care provider.

In various embodiments, Y-frame 100 has still other features that provide an ability for Y-frame 100 to be connected to still other hardware, such as other frames.

In an embodiment, Y-frame 100 is constructed of a radiopaque material, such as a metal. Alternatively, Y-frame 100 is constructed of a radiolucent material, such as a polymer (polyetheretherketone, carbon fiber, etc.). In some embodiments where Y-frame 100 is constructed of a radiolucent material, Y-frame 100 contains radiopaque markers in desired places. In various embodiments, such radiopaque markers are pins or spheres of metal or a similar radiopaque material, and are press-fitted into known places in Y-frame 100.

Pin-Holding Assembly

Figure 7:
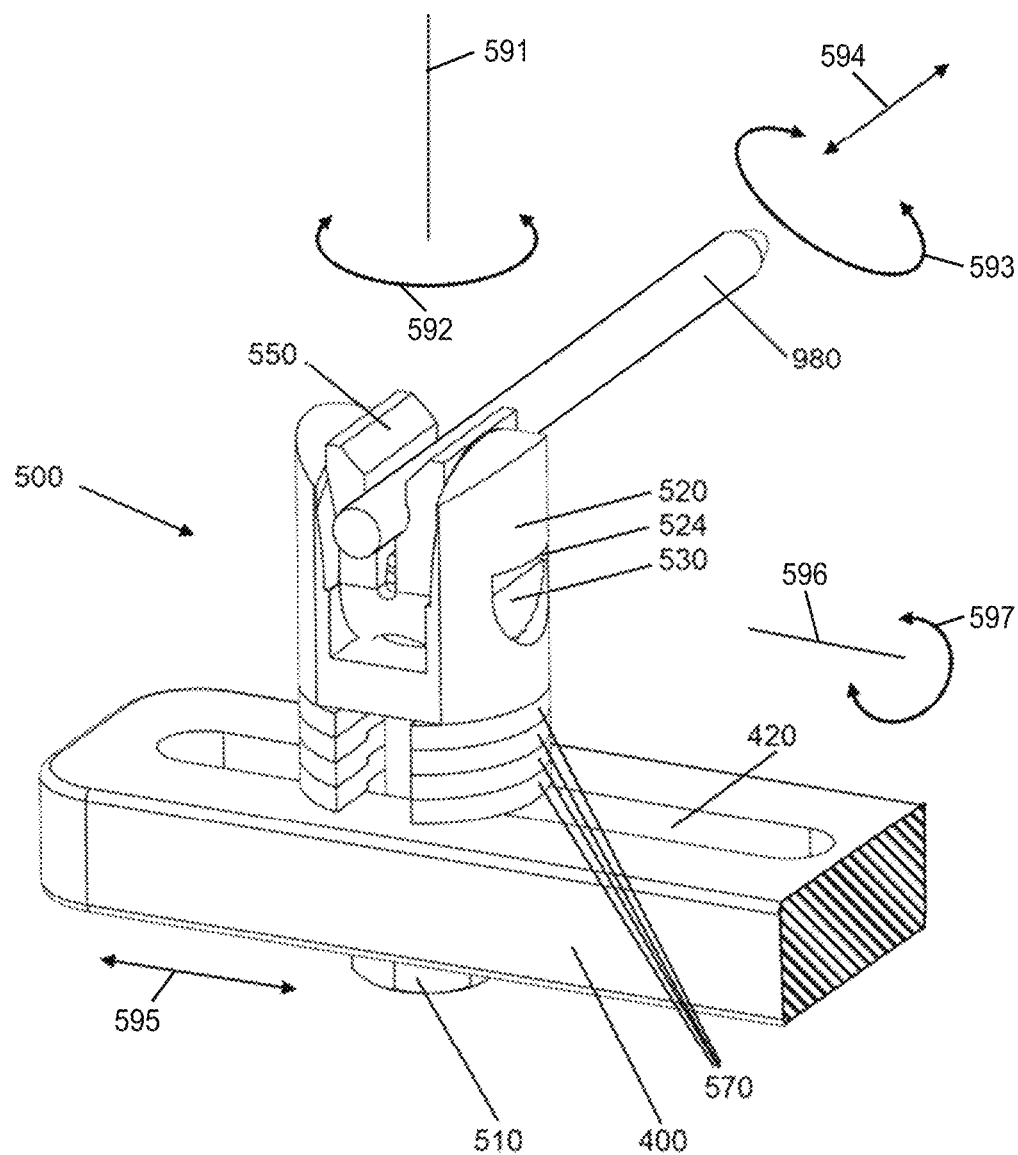
FIG. 7 is a top perspective view of a pin-holding assembly suitable for use in the Y-frame of FIG. 1.
Figure 8:
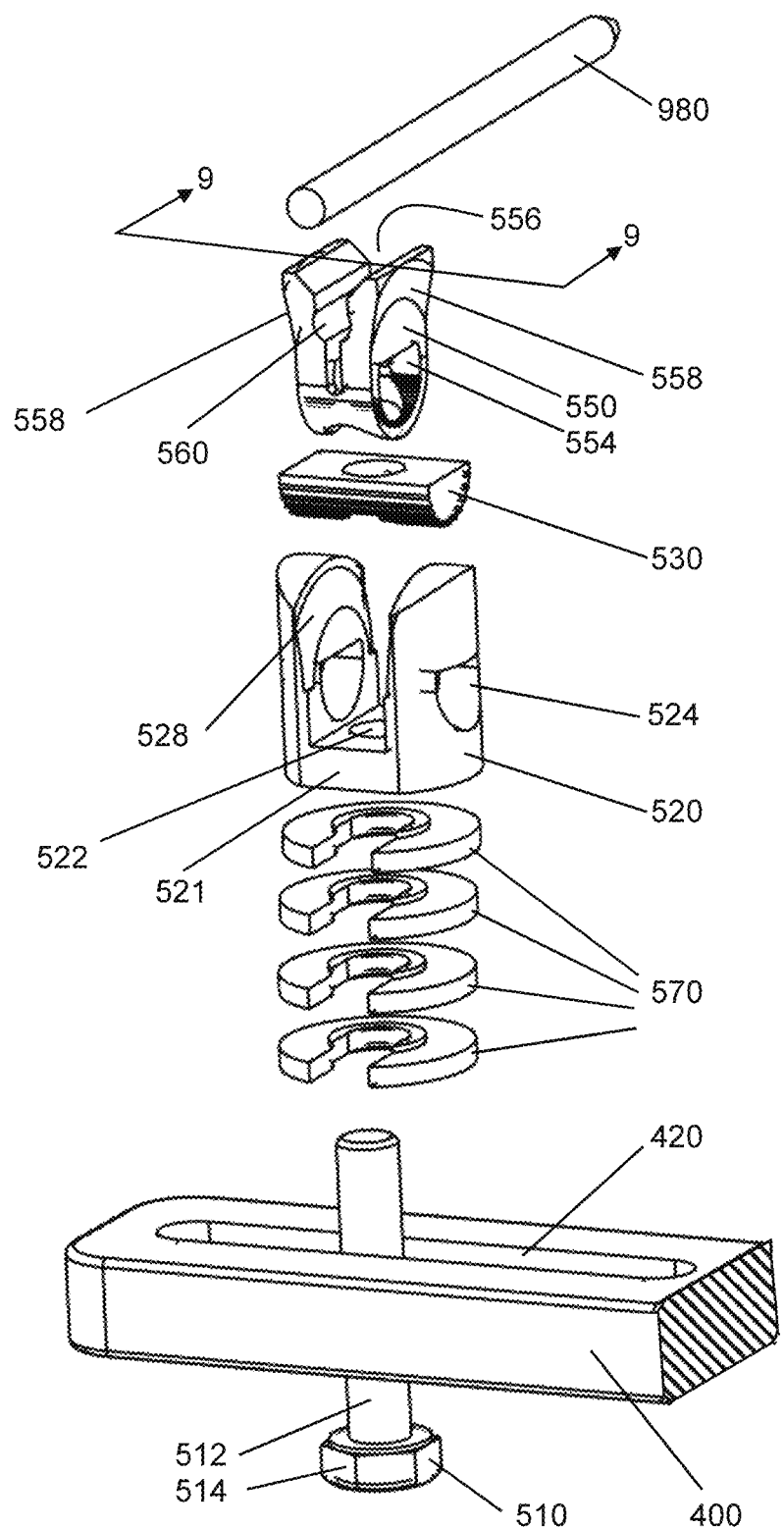
FIG. 8 is an exploded view of the pin-holding assembly of FIG. 7.

Reference is now made to FIG. 7 and FIG. 8. In embodiments of the invention, there may be provided a pin-holding assembly 500 that is attachable to any of superior arm 200, anterior arm 300 or posterior arm 400 as desired. In an embodiment, pin-holding assembly 500 moveably and insertably engages with slots 220, 320, 420. In an embodiment, pin-holding assembly 500 provides for the rigid attachment of a pin (such as a fixation pin 980 as illustrated or a transfixion pin) to any of the arms 200, 300, 400, while allowing adjustability of the orientation and position of the pin prior to tightening of pin-holding assembly 500. A single pin-holding assembly 500 is illustrated herein as being provided respectively on anterior arm 300 and on posterior arm 400, although pin-holding assemblies 500 could be provided on any arm in any combination, and/or in any quantity.

In an embodiment, pin-holding assembly 500 comprises bolt 510, which passes through yoke 520. In an embodiment, bolt 510 is dimensioned such that its shaft 512 passes through slots 220, 320, 420 but its head 514 does not pass through those slots.

In an embodiment, yoke 520 has a yoke axial bore 522, through which shaft 512 of bolt 510 passes. In an embodiment, yoke 520 also has a yoke cross bore 524, which intersects yoke axial bore 522 and is generally perpendicular to yoke axial bore 522. In an embodiment, yoke cross bore 524 has a circular shape in its lower region, but is illustrated as having a flat shape in its upper region. In an embodiment, yoke 520 has, on its external surface, a pair of opposed flats 521, which are parallel to each other and are suitable to be gripped by a wrench for purposes of tightening and untightening the connection, using bolt 510, of the pin-holding assembly 500 to arms 200, 300, 400.

Figure 9:
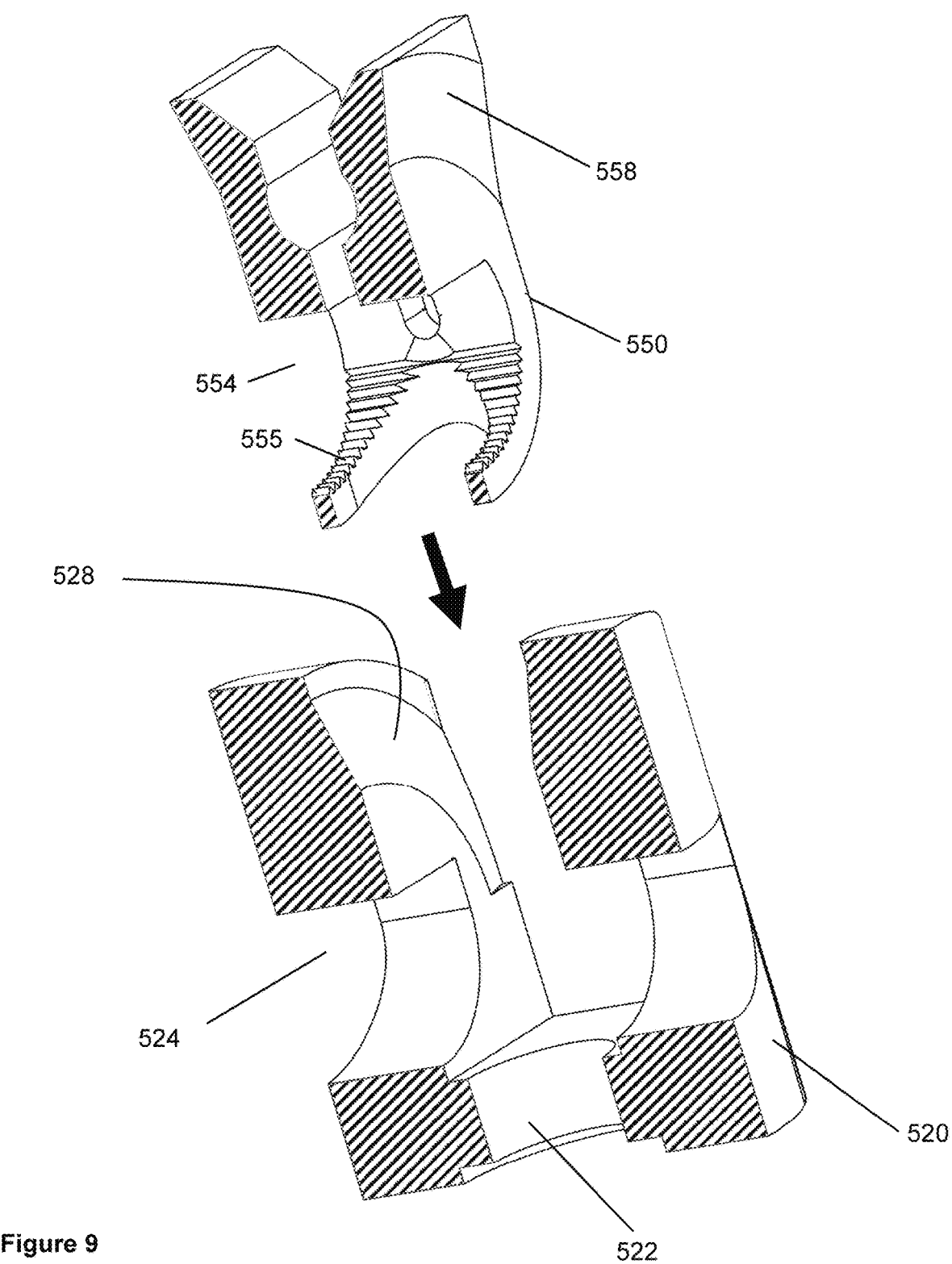
FIG. 9 is a top exploded perspective cross-sectional view of the yoke and the clamp of the pin-holding assembly, illustrating a wedging action.

In an embodiment, yoke 520 also has, in its upper region, an internal taper 528. In an embodiment, internal taper 528 is a segment of a conical surface. Such configuration may help to achieve a wedge action that causes clamp 550 to grasp a pin. This is shown in particular detail in FIG. 9.

In an embodiment, pin-holding assembly 500 comprises rocker nut 530. In an embodiment, bolt 510 threads into rocker nut 530. In an embodiment, rocker nut 530 has threaded hole 532 therethrough suitable to engage with bolt 510. In an embodiment, when tightened, bolt 510 urges rocker nut 530 toward the head 514 of bolt 510 and toward whichever arm 200, 300, 400 pin-holding assembly 500 is mounted on. In an embodiment, such action secures pin-holding assembly 500 onto respective arm 200, 300, 400 and also secures clamp 550 and may secure a fixation pin 980 or transfixion pin in clamp 550.

In some embodiments, pin-holding assembly 500 further comprises clamp 550. In an embodiment, clamp 550 has therethrough a clamp cross-bore 554. In some embodiments, yoke cross-bore 524, clamp cross-bore 554 and rocker nut 530 are all shaped such that clamp 550 is allowed to rotate through a range of angles (around the axis of yoke cross-bore 524) but at the end of that range of angles, rotation is limited by the non-circular portion of clamp cross-bore 554 bumping into rocker nut 530. In one embodiment, clamp 550 has a central slot 556 that is generally perpendicular to clamp cross-bore 554, opening upwardly in the illustrated orientation, such that slot 556 divides clamp 550 into two halves that are bendably connected to each other by the remaining non-slotted portion of clamp 550. As a result, in an embodiment, the two sides of clamp 550 have some ability to flex toward or away from each other so as to grasp a pin. In one embodiment, clamp 550 also has therethrough a partial channel 560 that intersects slot 556 and is partially defined by a concave shape in each of the two halves of clamp 550, and is suitable to hold a fixation pin 980 or transfixion pin.

Prior to tightening, a) pin-holding assembly 500 can rotate around the axis 591 of the bolt 510, as indicated at 592, b) fixation pin 908 can rotate around its own longitudinal axis, as indicated at 593, and can translate along its own longitudinal axis, as indicated at 594 and c) bolt 510 and pin-holding assembly 500 can slide in slot 420, as indicated at 595. In addition, rocker nut 530 allows rotation around the axis 596 of yoke cross bore 524, as indicated at 597.

In one embodiment, clamp 550 has, on its exterior, an external taper 558. In one embodiment, external taper 558 is conical. In one embodiment, the conical shape corresponds to internal taper 528, which is also conical. In one embodiment, external taper 558 cooperates with internal taper 528 of yoke 520 to provide a wedging action that urges the two halves of clamp 550 toward each other to grasp a fixation pin or transfixion pin. The conical nature of external taper 558 and internal taper 528 allows bolt 510 to exert pulling force that creates a wedge action for any of a variety of angular orientations of clamp 550 relative to rocker nut 530. This is particularly illustrated in FIG. 9.

Figure 10:
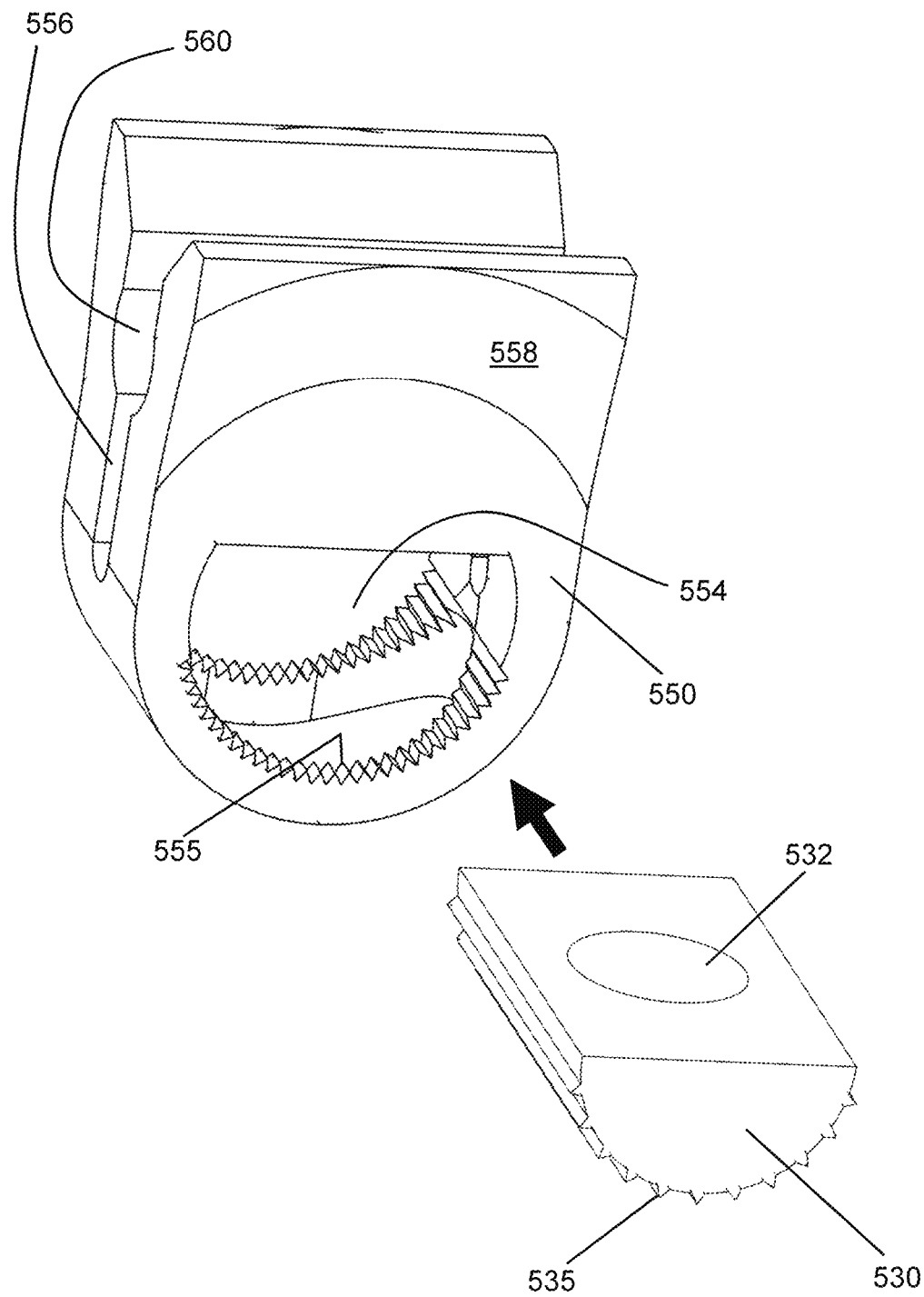
FIG. 10 is a top perspective view of the clamp and the rocker arm, separated from each other, illustrating engagement of respective teeth with each other.

Referring now to FIG. 10, in an embodiment, rocker nut 530 has an exterior surface that is generally shaped like a portion of a cylinder, such as a half-cylinder, with teeth 535 projecting from it. In one embodiment, such teeth 535 project along the entire length of rocker nut 530. In one embodiment (not shown), yoke cross-bore 524 is larger than the exterior of rocker nut 530 including its teeth 535, and the interior of yoke cross-bore 524 is free of teeth. In one embodiment, clamp cross-bore 554 comprises teeth 555 that are suitable to engage with the teeth 535 on the exterior surface of rocker nut 530. It is not necessary that the angular spacing between adjacent teeth of one set of teeth be identical to the angular spacing between teeth in the other set of teeth. Rather, in an embodiment, it is simply desirable that the angular spacing of one set of teeth be an integer multiple of the angular spacing of the other set of teeth. As illustrated in FIG. 10, the tooth-to-tooth angular spacing of teeth 555 on the clamp cross-hole 554 is one-third of the tooth-to-tooth angular spacing of teeth 535 on the rocker nut 530. As far as the extent along the axial direction of the rocker nut 530, the axial extent of teeth 555 on the inside of clamp cross-hole 554 need not be the same as the axial extent of teeth 535 on the rocker nut 530. In regard to the angular extent of the toothed regions, the angular extent of the toothed region inside the clamp cross-hole 554 does not have to be the same as (for example it could be smaller than) the angular extent of the toothed region on the rocker nut 530. It can be understood that for small angular extent of either toothed region, in combination with appropriate tooth dimensions, it may be possible to rotate rocker nut 530 within yoke cross-bore 524, after separating rocker nut 530 from clamp 550 generally along the lengthwise direction of bolt 510. On the other hand, for larger angular extent of both toothed regions in combination with appropriate tooth dimensions, change of angular position of rocker nut 530 might only be possible by sliding rocker nut 530 out of yoke cross-bore 524 along the axial direction of yoke cross-bore 524, rotating rocker nut 530 to a new angular orientation, and sliding rocker nut 530 back into yoke cross-bore 524.

Furthermore, although illustrations show arrays of teeth 535 and teeth 555, in some embodiments, that definition of angular position of clamp 550 relative to rocker nut 530 could be accomplished if one of those arrays of teeth were only a single-tooth suitable to engage the array of teeth on the other component. Furthermore, in an embodiment, if the surface of one of the components (rocker nut 530 and clamp cross-bore 554) were smooth rather than toothed, even if the other component's surface remained toothed, there could be continuous adjustment of angular position of clamp 550 relative to rocker nut 530 and yoke 520.

Figure 11:
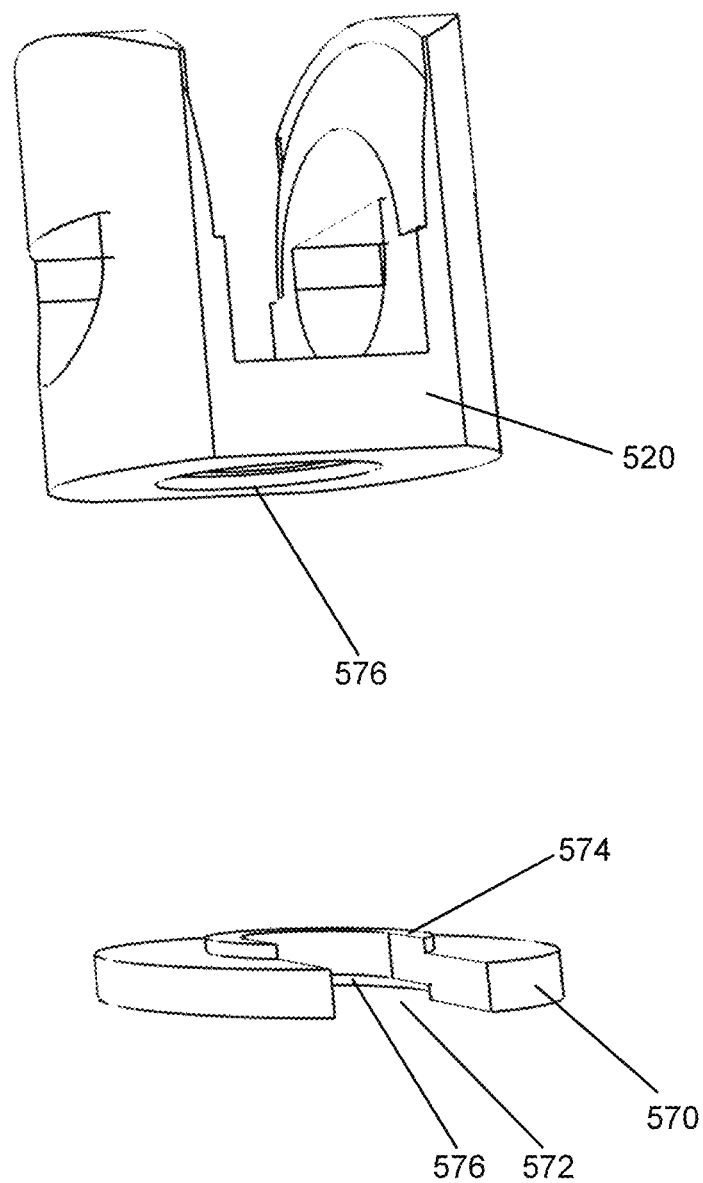
FIG. 11 is a bottom perspective view of a shim washer and a yoke, separated from each other, illustrating their interaction.

Referring now to FIGS. 7, 8 and 11, in various embodiments, one or more shim washers 570 are used to adjust overall elevation of the pin-holding assembly 500 (or, more precisely, the location of the gripped pin in a direction perpendicular to the surface of arm 200, 300, 400). In various embodiments, any desired number of shim washers 570 may be used, or none at all. In various embodiments, shim washers 570 are identical or have various different thicknesses such as to permit both fine and coarse adjustment. In one embodiment, shim washers 570 are U-shaped having a slot 572, so that they can be slipped onto or off of the stack of shim washers 570 without disassembling bolt 510 from rocker nut 530. In one embodiment, shim washers 570 have a raised feature 574 on one surface and, on an opposed surface, a corresponding recessed feature 576 suitable to nest with raised feature 574. The nesting features (raised feature 574 and recessed feature 576) of shim washers 570 are illustrated in FIG. 8. In one embodiment, yoke 520 has on its underside (shim-washer-facing surface) a recessed feature 576 suitable to mate with raised feature 574 on shim washer 570. This is illustrated in FIG. 11. Raised feature 574 and recessed feature 576 are shown as being axisymmetric, but if desired they could have a more complicated non-axisymmetric shape. In an embodiment, the interaction of raised feature 574 and recessed feature 576 helps to keep the stack of shim washers 570 assembled during trial fitting operations. In one embodiment, a bolt 510 is chosen whose length is appropriate for the number and dimensions of shim washers 570 used. In one embodiment, bolts 510 of varying lengths are provided. In various embodiments, in order to accommodate different lengths of bolt 510, the bolt-receiving threaded bore 532 through rocker nut 530 extends through the entirety of rocker nut 530, and there is provided empty space inside yoke 520 above rocker nut 530 in the indicated orientation. However, in an embodiment, above that empty space, sufficiently narrow space is provided so that bolt 510 cannot actually touch a pin (fixation pin 980 or transfixion pin 1000) that is grasped by pin-holding assembly 500. Such touching, if it were to occur, might act undesirably to urge a pin 980 or 1000 out of its grasped arrangement within clamp 550.

As illustrated in FIGS. 1-6, the slots 320, 420, 520 are of uniform cross-section along their lengths, except near their curved ends. As also illustrated in these Figures, the pin-holding assembly 500 and the bolt 510 interact with the slots 220, 320, 420 in such a way that the translational position of pin-holding assembly 500 in slots 220, 320, 420 is chosen from a continuous range. However, there also are other possibilities involving discrete translational positions.

Figure 12:
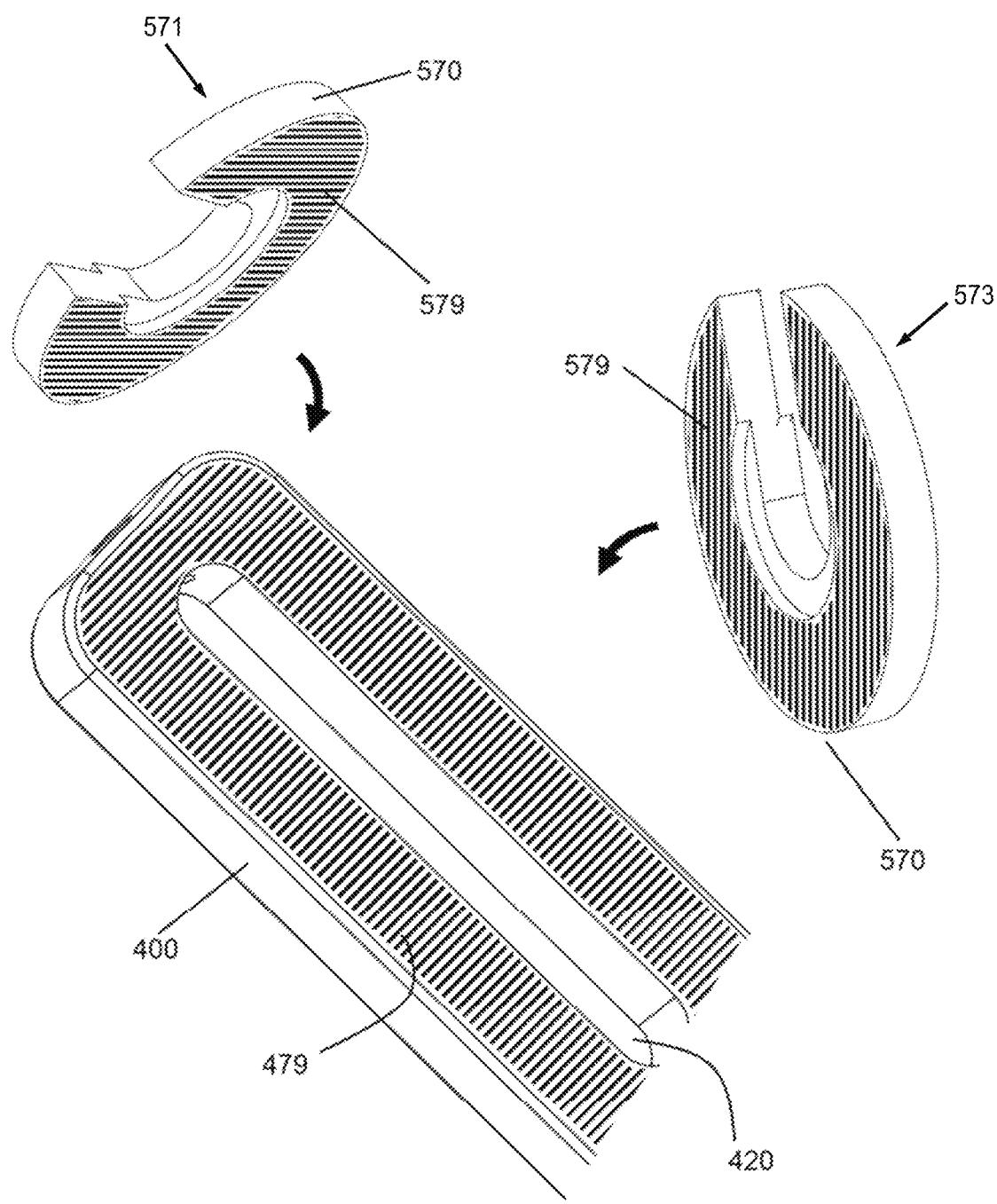
FIG. 12 is a partial perspective view of an arm having grooves on a surface, and its interaction with a shim washer.

Referring now to FIG. 12, in some embodiments, any one or more of arm surfaces adjacent to slots 220, 320, 420 include ridges 479 that are spaced at uniform intervals, and such ridges 479 encourage or require the pin-holding assembly 500, when tightened, to occupy one of the positions defined by the ridges 479. For example, in one embodiment, shim washers 570 have, on their undersides, ridges 579 that are complementary to the ridges 479 on the arms 200, 300, 400. If the shim washer 570 has an appropriate angular orientation, the ridges 579 on the shim washer 570 can engage with the ridges 479 on the surface of the arm so, as to define discrete translational positions. If the shim washer 570 has a different angular orientation, such as an orientation where the respective ridges 479, 579 are oriented approximately perpendicular to each other, ridges 579 and ridges 479 will not engage with each other and continuous adjustment of translational position will be possible. Of course, depending on the wishes of the user, it would also be possible to use a shim washer 570 having a smooth underside, which would provide continuous adjustment of translational position even if there are ridges 479 on the arm 200, 300, 400.

FIG. 12 shows at 571 an engaging orientation for washer 570 and further shows at 573 a non-engaging orientation for washer 570.

Similar considerations apply to yoke 520 and its underside surface. If no shim washers 570 are used, the underside surface of yoke 520 contacts a surface of arms 200, 300, 400 in various embodiments. In an embodiment, such underside surface of yoke 520 could be either smooth or grooved. If grooved, in an embodiment, such surface could result in a constraint against rotation of pin-holding assembly 500 around the axis of bolt 510, in addition to constraining the translational position to discrete locations along the length of slot 220, 320, 420.

Figure 13:
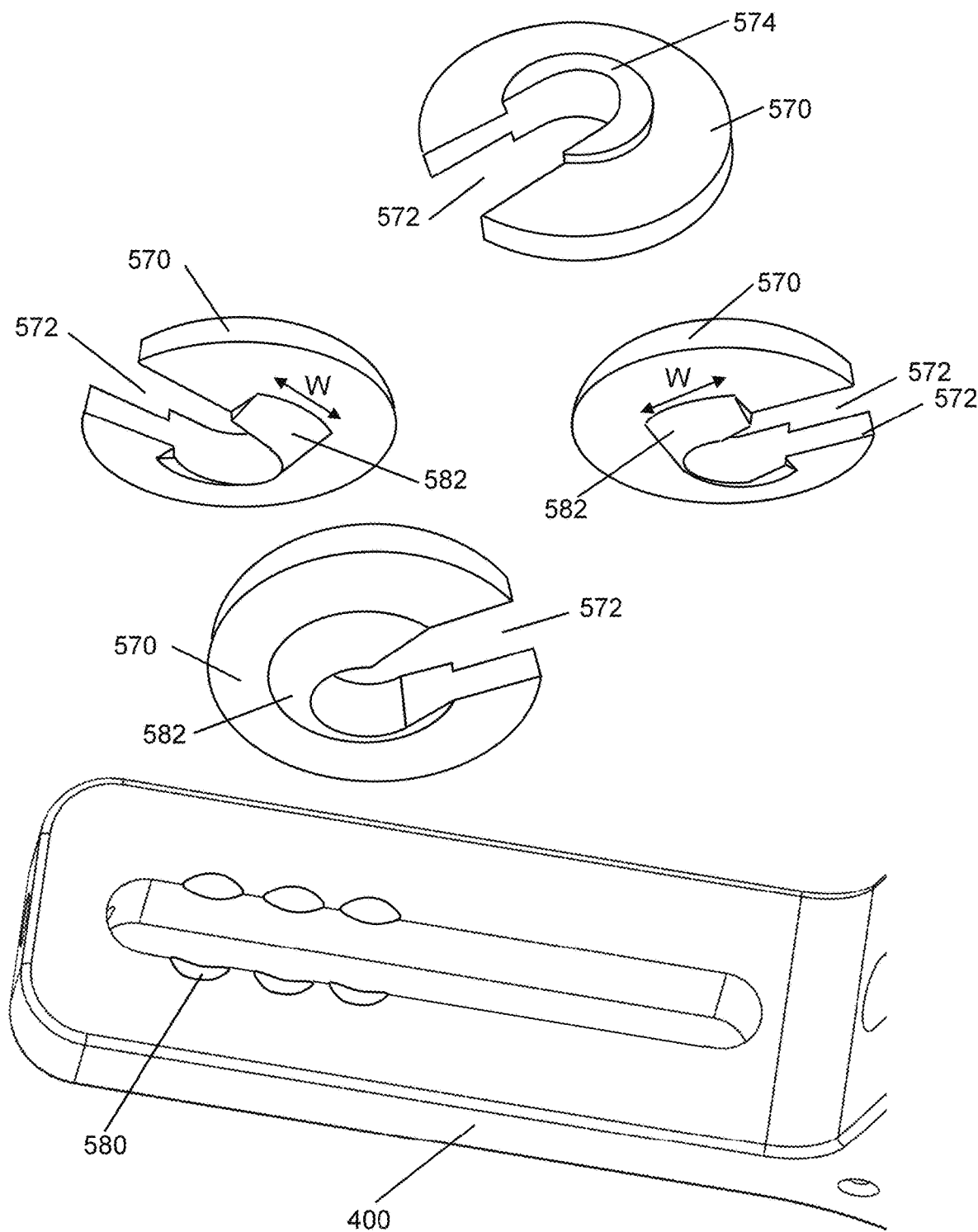
FIG. 13 is a partial perspective view of an arm having countersinks, and its interaction with a shim washer.

Referring now to FIG. 13, in another embodiment, arms and slots such as slots 220, 320, 420 have discrete features along them in the form of dished shapes such as countersinks 580, and the underside of shim washers 570 or of yoke 520 has features 582 complementary to the countersinks 580. In an embodiment, choice between discrete and continuous positioning could be made by the choice of using shim washers 570 that either have a flat bottom (which would avoid interaction with the countersinks 580) or have on their bottom a protrusion 582 that engages with the countersinks 580. For engaging with countersinks 580, in one embodiment, the protrusions 582 are conical. In FIG. 13, one of the shim washers 570 is illustrated as having a conical protrusion 582 around a full circumference of a cone (except where the washer 570 is slotted by slot 572). In an embodiment, such a protrusion 582 would engage a countersink 580 for any angular orientation of shim washer 570. As is also illustrated in FIG. 13, it is also possible that a shim washer 570 could have a conical protrusion 582 that is abbreviated from two opposed sides, such that the remaining conical protrusion 582 has a width W. For such a shim washer 570, in an embodiment, if the shim washer 570 is oriented in one angular position (with respect to the axis of the hole through shim washer 570), the protrusion 582 would engage with the countersink 580. For the same shim washer 570, in an embodiment, assuming that the remaining width W of the protrusion 582 is narrower than the width of the slot 220, 320, 420, the protrusion 582 can reside within the slot 220, 230, 240 and avoid engaging the countersink 580. Such a situation, in an embodiment, would provide continuous adjustability of the translational position of pin-holding assembly 500 along arm 200, 300, 400.

In an embodiment, a pin-holding assembly 500 can be used to hold either a fixation pin 980 or a transfixion pin 1000. The use of a pin-holding assembly 500 with superior arm 200 is not illustrated, although in an embodiment a pin-holding assembly 500 could be so used if desired.

In an embodiment, pin-holding assembly 500 may provide at least the following degrees of adjustability. This adjustability can be provided with respect to arms 200, 300, 400

In translation along the length of arm 200, 300, 400, it is possible to adjust and then lock the position of pin-holding assembly 500 along the linear direction of slots 220, 320, 420. In some embodiments, this adjustment is illustrated as being continuous.

In translation perpendicular to the surface of arm 200, 300, 400, the position of pin-holding assembly 500 can be adjusted and then locked by the selection and use of shim washers 570. This adjustment can be discrete because of the use of discrete shim washers 570.

In a third translational direction, the position of pin 980 can be adjusted and then locked by sliding pin 980 along the length direction of pin 980, within clamp 550.

In regard to rotation around the axis of bolt 510, the orientation of pin 980 can be adjusted and then locked by rotating yoke 520 around the axis of bolt 510. As illustrated in FIG. 7, this adjustment is continuous.

In regard to rotation around the axis of yoke cross-bore 524, the orientation of pin 980 can be adjusted and then locked by rotating clamp 550 with respect to rocker nut 530 and yoke 520. It is illustrated that this adjustment is in discrete steps, but it is described that continuous adjustment also could be achieved.

In regard to rotation around the axis of pin 980, it is possible for pin 980 to be rotated and then locked with respect to that axis, but in practice this may be unnecessary or insignificant because of the axisymmetric nature of the overall features of pin 980.

Clamping Bolt

Figure 14:
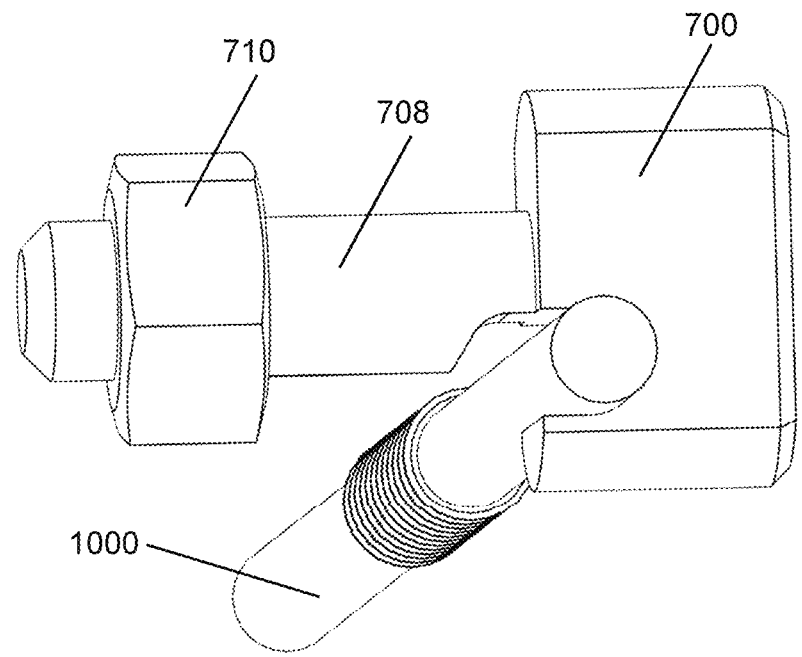
FIG. 14 is a perspective view of the superior transfixion pin and its clamping bolt.
Figure 15:
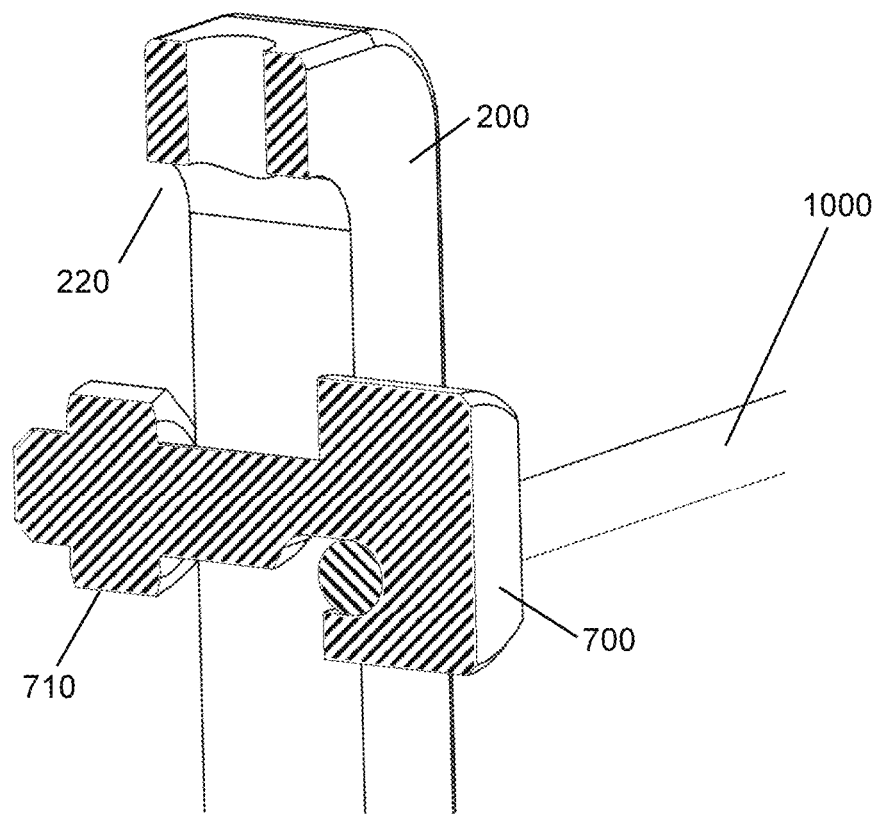
FIG. 15 is a cross-sectional view of the superior transfixion pin and its clamping bolt.
Figure 23:
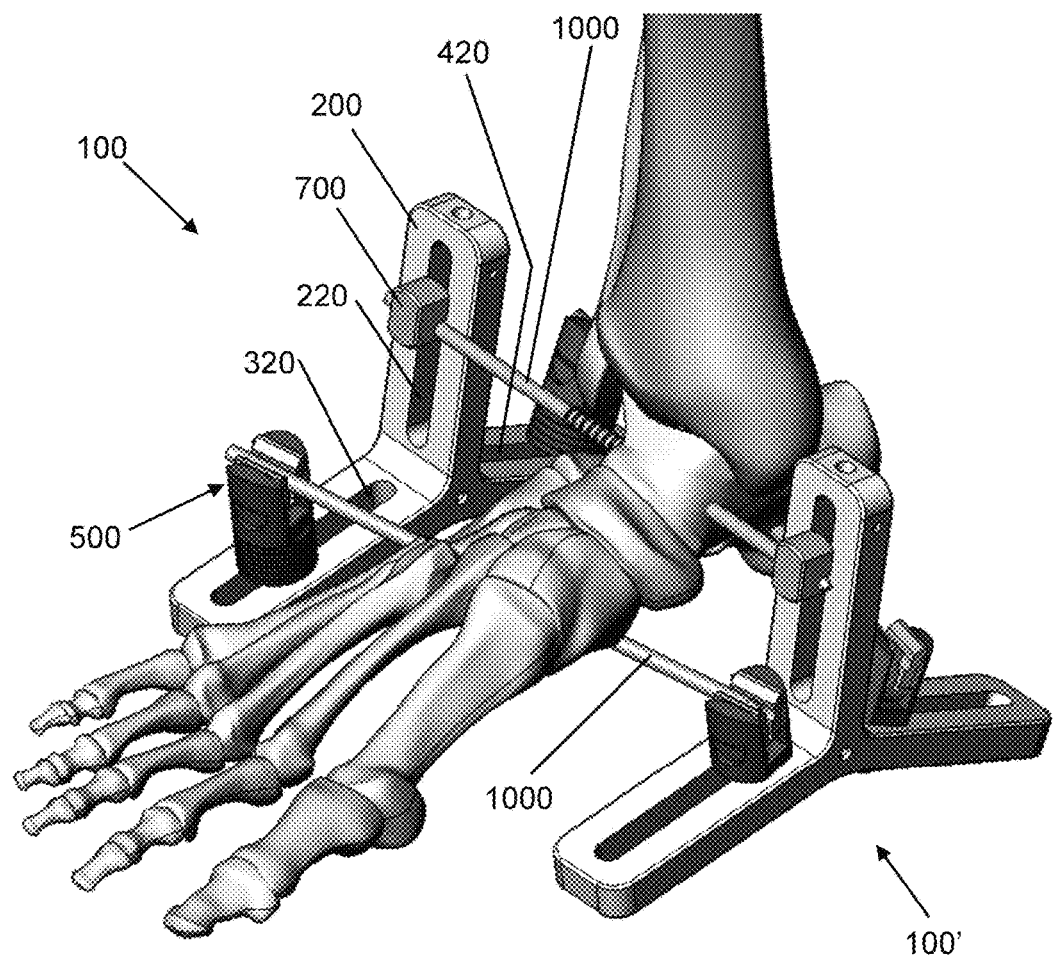
FIG. 23 is a top perspective view of a skeletal foot and ankle instrumented according to an embodiment of the invention.
Figure 24:
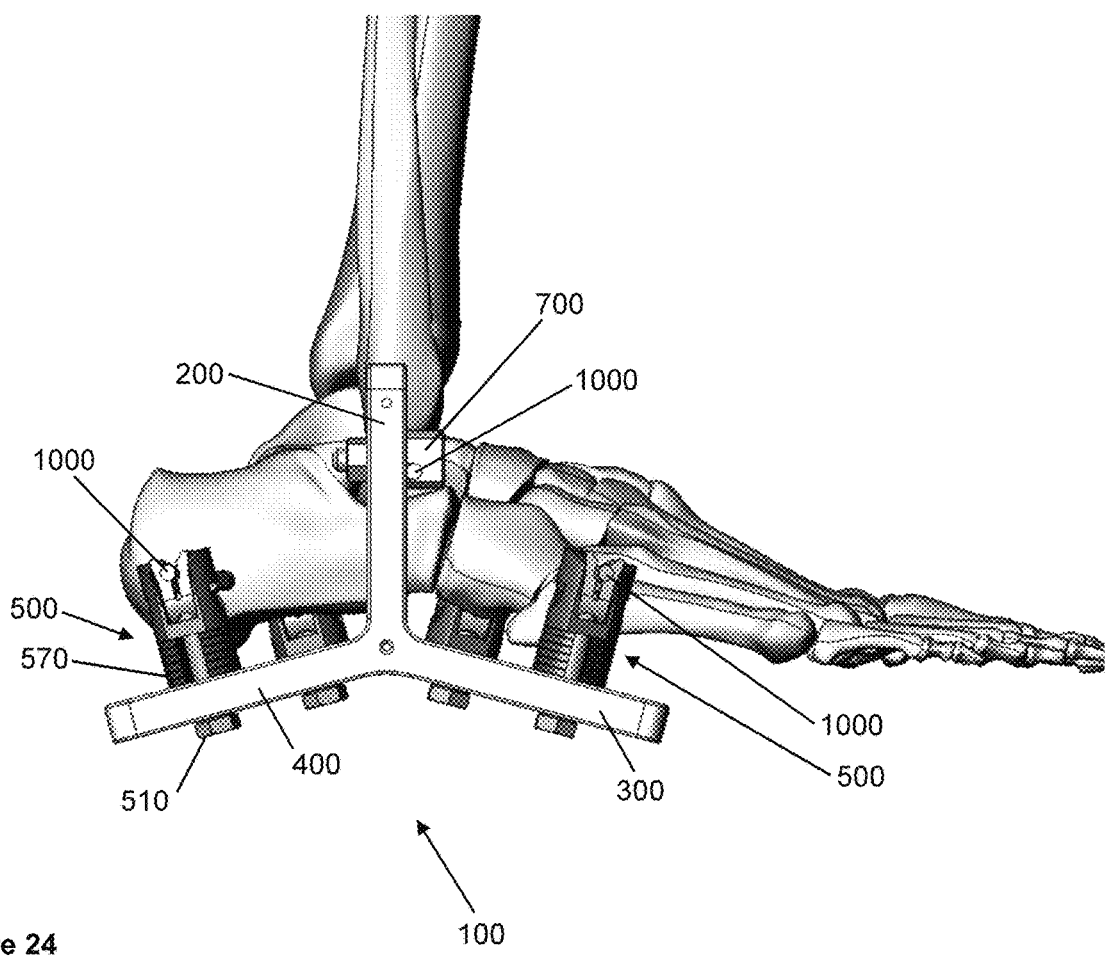
FIG. 24 is a side view corresponding to FIG. 23.

FIGS. 14-15 illustrate the use of a clamping bolt 700 to secure a transfixion pin 1000 to superior arm 200 of Y-frame 100. In one embodiment, this configuration and the use of clamping bolt 700 provides fewer degrees of adjustability (i.e., more degrees of constraint) than are provided by pin-holding assembly 500. In FIG. 15, clamping bolt 700 is shown engaging with superior arm slot 220 such that clamping bolt 700 urges the transfixion pin 1000 directly into contact with a flat surface of superior arm 200. In an embodiment, clamping bolt 700 engages with nut 710. It can be understood that if desired, instead of clamping a transfixion pin 1000, clamping bolt 700 could be used to clamp a fixation pin (not illustrated). In various embodiments, the pin-holding assembly 500 and clamping bolt 700 are used at the same time, as discussed below and as illustrated in FIGS. 23 and 24.

Bolt 700 may provide at least the following degrees of adjustability. This adjustability can be provided with respect to arms 200, 300, 400 although it is only illustrated with superior arm 200.

In translation along the length of arm 200, 300, 400, it is possible to adjust and then lock the position of pin-holding assembly 500 along the linear direction of slots 220, 320, 420. This adjustment is illustrated as being continuous.

Translational adjustment perpendicular to the surface of arm 200, 300, 400, adjustment is illustrated as not being possible; transfixion pin 1000 is constrained to touch the surface of arm 200, 300, 400.

In another translational direction, along the longitudinal direction of transfixion pin 1000, the position of pin 1000 can be adjusted and then locked by sliding transfixion pin 1000 along the length direction of transfixion pin 1000, within clamping bolt 700.

In regard to rotation around the axis of the arm (such as axis 210 of arm 200), transfixion pin 1000 is constrained to be in contact with the flat surface of the arm. This eliminates a degree of freedom of adjustment that roughly corresponds to the degree of freedom of rotation that, in pin-holding assembly 500, was provided by rotation of clamp 550 with respect to rocker nut 530.

In regard to rotation around the axis of clamping bolt 700, as illustrated in FIGS. 14-15, adjustment is permitted of this angular position. This roughly corresponds to the degree of freedom of rotation that, in pin-holding assembly 500, was provided by rotation of pin-holding assembly 500 around the axis of bolt 510. However, elsewhere herein there is described an alternative design of clamping bolt 700 that imposes a constraint in this regard.

In regard to rotation around the axis of transfixion 1000, it is possible for transfixion pin 1000 to be rotated and then locked with respect to that axis, but in practice this may be unnecessary or insignificant because of the axisymmetric nature of the overall features of transfixion pin 1000.

Figure 16:
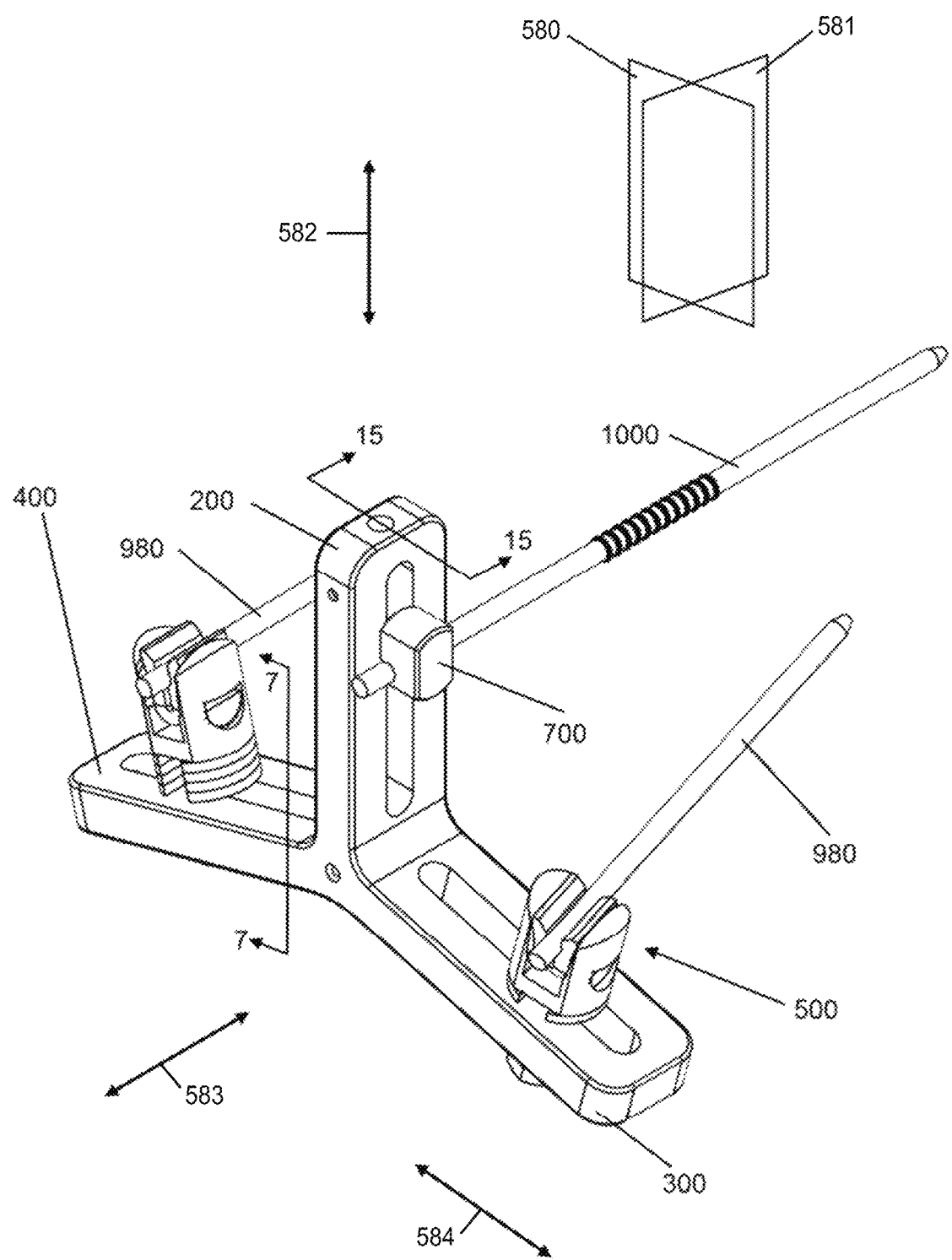
FIG. 16 is a top perspective view of the Y-frame of FIG. 1, together with gripping hardware in each arm and a superior transfixion pin and an anterior fixation pin and a posterior fixation pin.

FIG. 16 illustrates a Y-frame 100 in combination with mounting hardware on each arm 200, 300, 400. In particular, FIG. 16 shows a transfixion pin 1000 attached to superior arm 200 by clamping bolt 700, and fixation pins 980 attached to anterior arm 300 and posterior arm 400 by pin-holding assemblies 500. It can be understood that in embodiments it is possible to attach either a fixation pin 980 or a transfixion pin 1000 to any of arms 200, 300, 400 using either a pin-holding assembly 500 or a clamping bolt 700. Any quantity of such transfixion pins 1000, fixation pins 980, and clamping bolts 700 and pin-holding assemblies 500 can be used on any arm 200, 300, 400, as may be desirable for the needs of a particular patient.

Y-Frame Having Arms that Permit Rotation Around Long Axis of Respective Arm

In embodiments illustrated in FIGS. 1-6, the arms 200, 300, 400 are substantially rigidly connected to each other, having fixed positions relative to each other. In another embodiment of the invention, the arms 200, 300, 400 allow adjustment of an angle that can be referred to herein as an arm twist angle, and such motion can be referred to as arm twisting. This arm twist angle can refer to rotation around of one portion of the arm 200, 300, 400, with respect to another portion of the same arm or with respect to a central region 116 of the Y-frame 100. Such rotation can be rotation around an axis such as superior arm axis 210, anterior arm axis 310, posterior arm axis 410.

Figure 17:
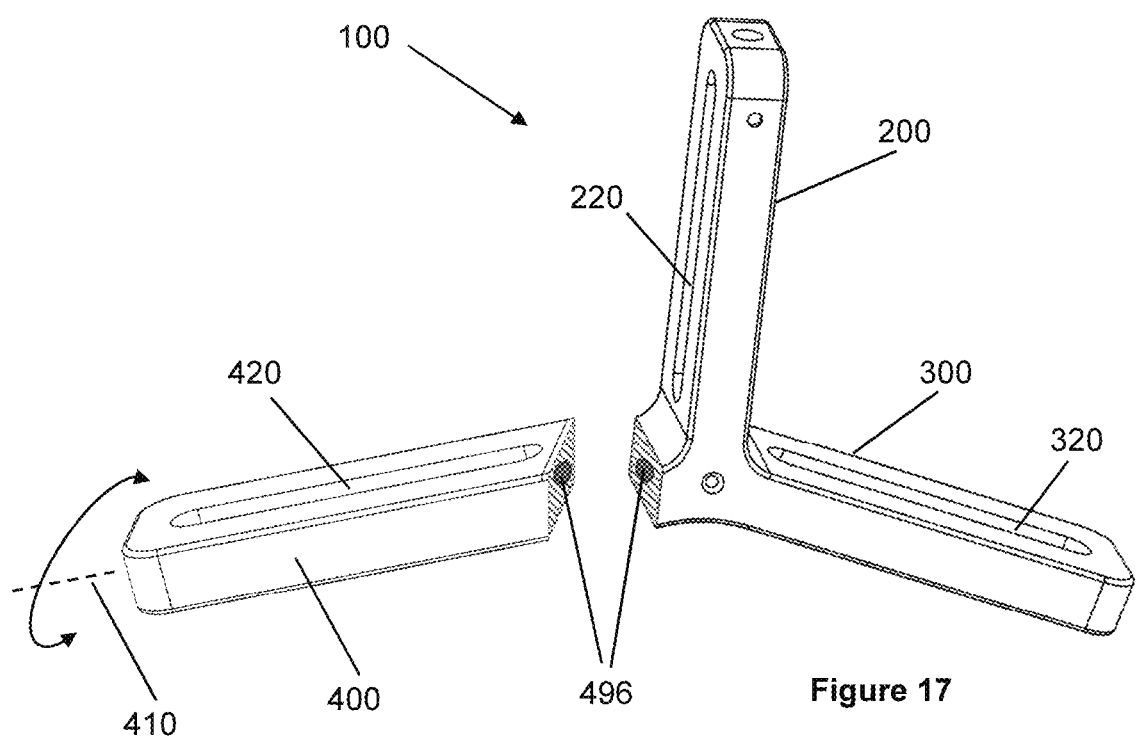
FIG. 17 is a top perspective exploded view of another embodiment of a Y-frame having the ability to adjust the twist angles of one of the arms.

Referring now to FIG. 17, there is shown an embodiment of the Y-frame 100 that allows adjustment of arm-twist angle independent of any other adjustment. Such adjustment may be provided by twisting pivot 496. Twisting pivot 496 is shown as being located between slot 420 and the central region of Y-frame 100. In an embodiment, there may be provided a locking or tightening mechanism for locking twisting pivot 496. In one embodiment, detents are also provided in this rotation, if desired.

Y-Frame Having Arms that can Angulate with Respect to Each Other

In further embodiments of the invention, it is possible to provide angular adjustability of arms 200, 300, 400 in an angular direction that is within the plane of arms 200, 300, 400 (assuming that axes 210, 310, 410 of arms 200 300, 400 are coplanar). These angles can be referred to herein as arm rotational angles and the motion can be referred to herein as angulation.

Figure 18:
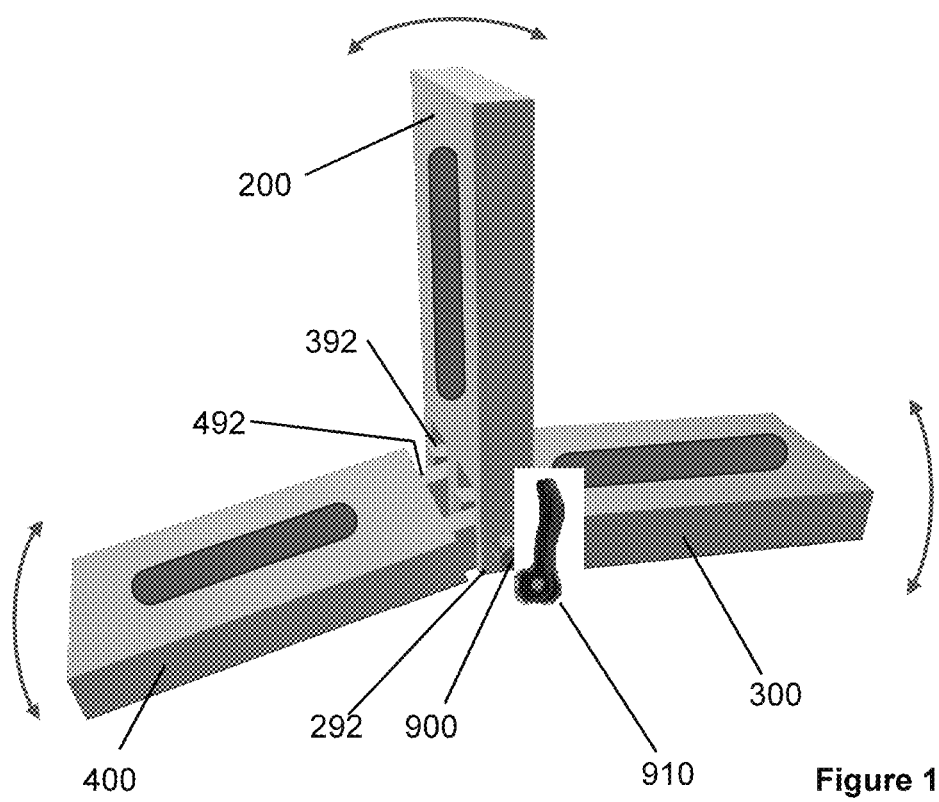
FIG. 18 is a top perspective view of another embodiment of a Y-frame having separate arms, having the ability to adjust within a range, the angulation of the arms within the plane of the Y-frame.

For example, as illustrated in FIG. 18, in an embodiment there is provided a common hinge such that arms 200, 300, 400 all rotate around Y-frame axis 110. As illustrated, superior arm 200 has superior arm finger projections 292, anterior arm 300 has anterior arm finger projections 392 and posterior arm 400 has posterior arm finger projections 492. In an embodiment, these finger projections 292, 392, 492 have respective holes therethrough that align with each other, and a hinge pin 900 is provided that fits through those holes to create the hinge.

In various embodiments, finger projections 292, 392, 492 fit among each other with a close but freely moving fit, and finger projections 292, 392, 492 have a desired degree of ability to deflect relative to each other along the axis of hinge pin 900. Furthermore, in an embodiment there may be provided a clamping device 910 such as a cam clamp that is suitable to exert force urging the finger projections 292, 392, 492 into contact with each other so as to lock the relative angular positions of arms 200, 300, 400.

For example, in an embodiment, the clamping device 910 creates tensile force in hinge pin 900 and that tensile force is used to urge all of the finger projections 292, 392, 492 compressively into contact with each other. In one embodiment, finger projections 292, 392, 492 are designed with an appropriate amount of flexibility so as to allow enough deflection to achieve the desired locking upon application of force by clamping device 910. Such contact is frictional contact in one embodiment. Such contact may be enhanced with surface roughness as desired in one embodiment. In one embodiment, clamping device 910 is or includes a cam with a handle to cause rotation of the cam in order to urge finger projections 292, 392, 492 into contact with each other.

The arrangement illustrated in FIG. 18 is capable of continuous adjustment over a range of angles between arms 200, 300, 400. As an alternative, in an embodiment, the angles that are permitted or are allowed or accessible are certain discrete angles. This can be achieved with the illustrated hinge arrangement if appropriate surfaces of finger projections 292, 392, 492 that face each other have grooves or serrations, such radially oriented serrations centered at the hinge axis of hinge pin 900. Thus, when the arms 200, 300, 400 are not locked to each other, there is ability of the finger projections 292, 392, 492 to rotate relative to one another around the axis of hinge pin 900, so as to allow relative rotation of the arms 200, 300, 400. In alternate embodiments, there is an incentive for the arms 200, 300, 400 to settle into certain discrete angular positions. In one embodiment, these discrete angular positions are spaced at equal angular intervals. In one embodiment, spring loading along the axis of the hinge pin 900 is used to govern the ease or difficulty of moving among the permitted angular positions, creating detents for the rotation.

Apparatus Having Interchangeably Connectable Hub and Arms

FIGS. 19-22 illustrate further embodiments of the Y-frame that include other ways of achieving angular adjustment such as angulation or arm-twisting or both is to have a hub 800 such that arms 200, 300, 400 interact with a surface of the hub 800 and are joinable to hub 800. In various embodiments, the joining comprises respective locking screws or other mechanism through the sidewall 810 of the hub 800. The sidewall 810 of hub 800 can have appropriate slots for respective locking screws to pass through. The dimensional relationship between locking screws and slots can provide constraint on motion as desired.

Figure 19:
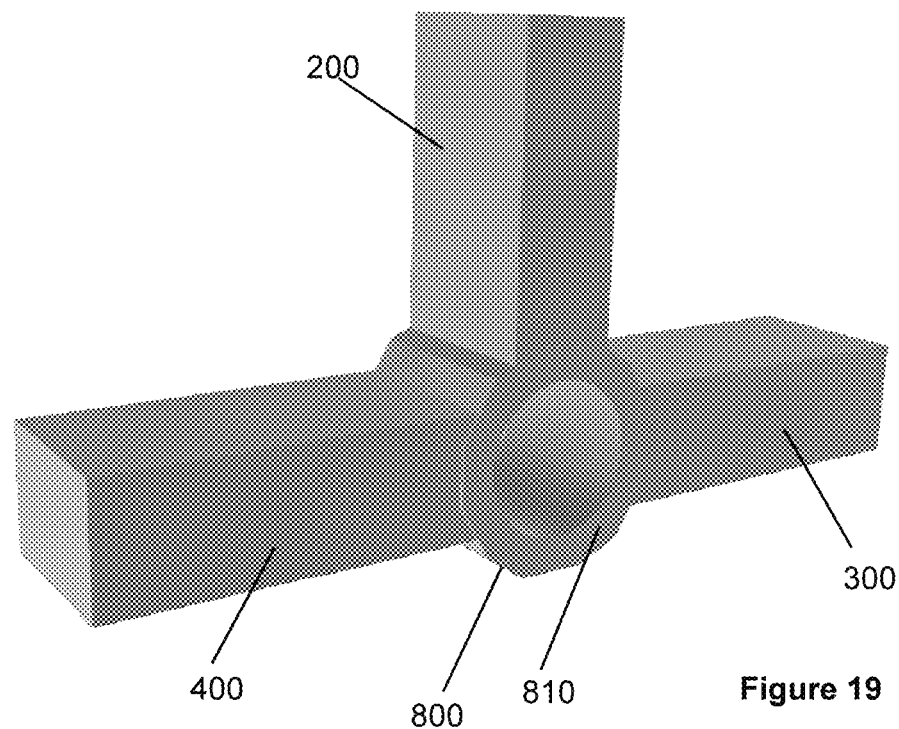
FIG. 19 is a top perspective view of another embodiment of a Y-frame having a hub and separate arms, having ability to adjust angulation of the arms within the plane of the Y-frame, with the possible angular positions being discrete positions.
Figure 20:
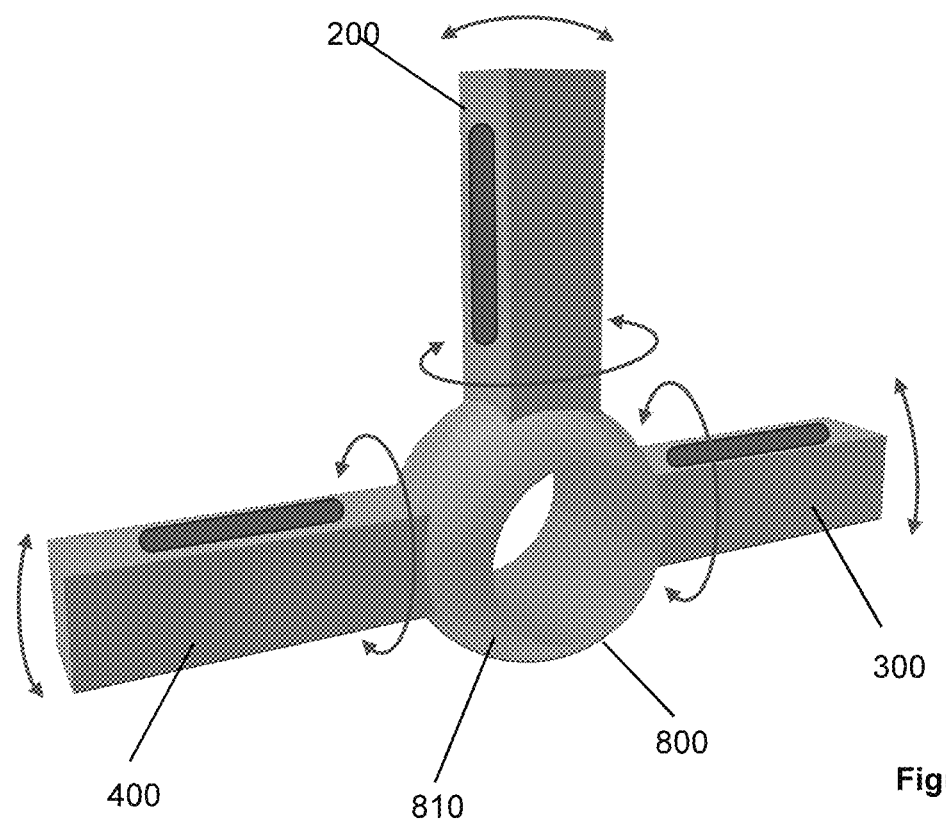
FIG. 20 is a top perspective view of a another embodiment of a Y-frame having a hub and separate arms, having ability to adjust, continuously within a range, the angulation of the arms within the plane of the Y-frame, and also the ability to adjust the twist angle of individual arms with respect to a respective longitudinal axis of the individual arm.

With the exception of grooves or similar features, in various embodiments, the surface of hub 800 is generally cylindrical or polygonal-prismatic (as shown in FIG. 19) or generally spherical (as shown in FIG. 20). In an embodiment, a generally cylindrical or polygonal prismatic hub 800 could prevent out-of-plane alignment of the various arms 200, 300, 400 and could require the arms 200, 300, 400 to be coplanar. In an embodiment, a constraint of the allowable rotational angles to discrete intervals could be achieved with polygonal facets on the surface of the hub 800. This is shown in FIG. 19. A less-constrained situation can be achieved with an externally spherical hub as shown in FIG. 20.

Figure 21:
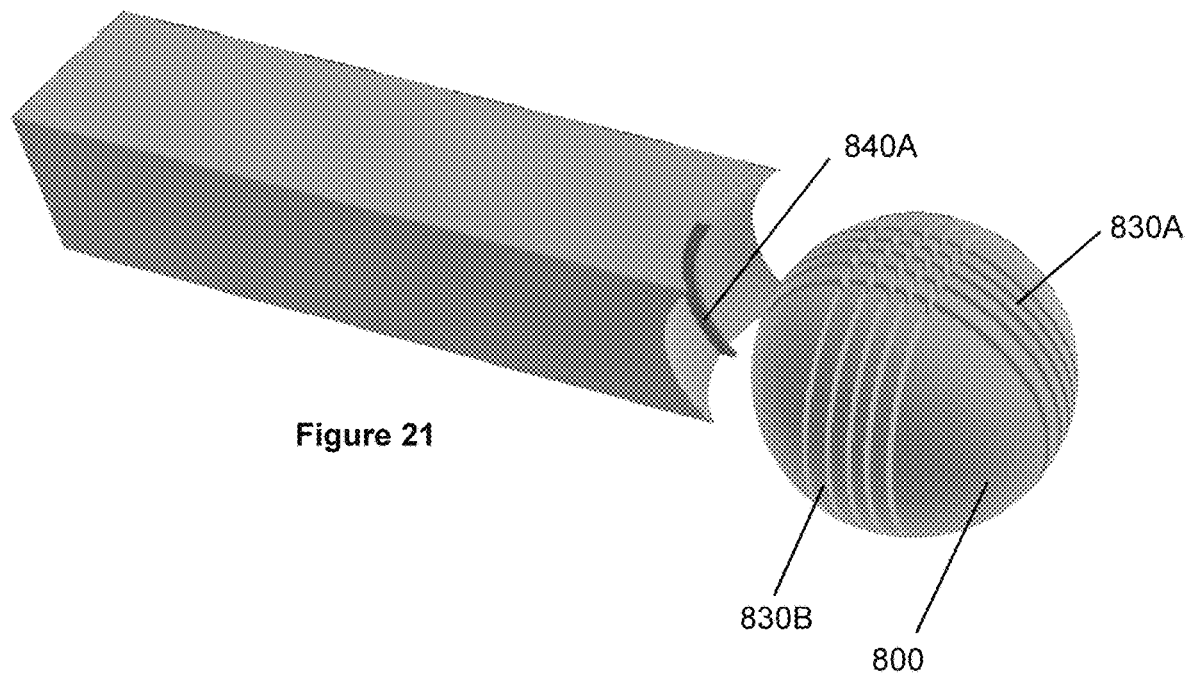
FIG. 21 shows an embodiment having grooves on a surface of a spherical hub and shows one arm with one type of groove-complementary feature.
Figure 22:
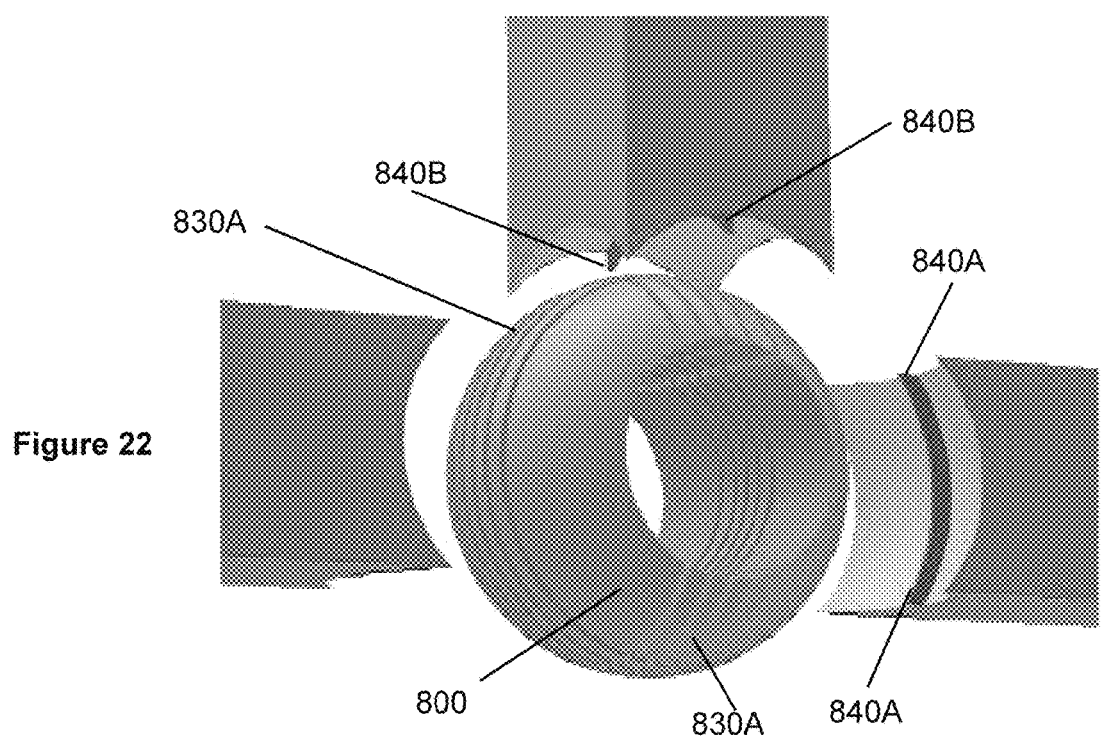
FIG. 22 shows an embodiment having grooves on a surface of a spherical hub and shows several arms with various groove-complementary features on the hub-facing surface of the arms.

As illustrated in FIGS. 21-22, the surface of the hub 800 can have grooves therein, in further embodiments of the Y-frame. In one embodiment, grooves are parallel to other similar grooves. In one embodiment, there are two different groups of grooves 830A, 830B that intersect each other generally perpendicularly. As one example, in such an embodiment, if the grooves 830A are in the plane of the rotational angles, and if the arms 200, 300, 400 engage with the grooves 830A, the grooves 830A may permit continuous angular motion of arms 200, 300, 400 among various rotational angles. At the same time, in such an embodiment, such grooves 830A may provide some degree of constraint with regard to other degrees of motion (such as the arm twist angle of respective arms 200, 300, 400). In such an embodiment, if grooves 830B are perpendicular to the plane of the rotational angles, and if the arms engage with the grooves 830B, the grooves 830B may discretize the achievable rotational angles. FIG. 22 shows one of the arms interacting with one set of grooves 830A based on a groove-complementary feature 840A oriented in one direction, and another of the arms interacting with the other grooves set of grooves 830B oriented in another direction with another appropriately oriented groove-complementary feature 840B.

In various embodiments, the hub-facing surface of the arms 200, 300, 400 has groove-complementary features such as teeth. In various embodiments, these features extend in one direction, or in two directions, or the hub-facing surface could be smooth and non-interacting with the grooves.

In various embodiments, discrete definition or adjustment of the angular positions can be achieved with the presence of grooves 830A, 830B on the surface of hub 800 and groove-complementary features 840A, 840B on the ends of arms 200, 300, 400. In various embodiments, if it is desired to have continuous rather than discrete adjustment of rotational angle, either situation is possible depending on the nature of the hub-facing surface of the arms. In various embodiments, different arms have different such characteristics if desired.

Certain reference directions are further shown in FIG. 16, including sagittal plane 580, coronal plane 581, superior-inferior (vertical) direction 582, medial-lateral direction 583, and anterior-posterior direction 584.

Additional Y-Frame, and Application to Foot

In an embodiment of the invention, a first Y-frame 100 can be used together with a second Y-frame 100' on the opposite side of an extremity such as a foot. As illustrated in FIGS. 23 and 24, the Y-frame 100 on one side of the foot is identical to the Y-frame 100' on the other side of the foot, although if desired the two Y-frames 100, 100' could differ from each other in some way. Pins such as fixation pins 980 or transfixion pins 1000 can enter the extremity from both sides of the extremity and can join to respective Y-frames 100, 100'.

FIGS. 23-24 illustrate application of embodiments of the invention to a foot. FIG. 24 is a side view of FIG. 23. As illustrated, in the Y-frame 100, the orientation of arms 200, 300, 400 with respect to each other is such that the superior arm 200 roughly aligns with the patient's leg, the anterior arm 300 roughly aligns with the forward part of the foot, and the posterior arm 400 roughly aligns with the heel of the foot. In an embodiment, the extent and positions of slots 220, 320, 420 correspond to locations of likely interest for placement of pins for fixation of particular bones in the foot. In FIGS. 23-24, all three of the illustrated pins are transfixion pins 1000. In an embodiment, one of the transfixion pins 1000 is held by clamping bolt 700, and two others are held by pin-holding assemblies 500. This is a slightly different use of pins, compared to what is illustrated in FIG. 16. In general, any type of pin (fixation pin 980 or transfixion pin 1000) can be used with either type of support (pin-holding assembly 500 or clamping bolt 700) on any arm (200, 300, 400).

Relative Geometric Orientation of Respective Y-Frames

Reference is now made to FIGS. 25-33, in which the fixation apparatus contains two identical Y-frames 100, 100' of the type illustrated in FIGS. 1-6.

In embodiments of the invention, there may be provided various geometric constraints among certain components. In some embodiments there is a transfixion pin 1000 extending between two Y-frames 100, 100' and rigidly attached to each of the Y-frames 100, 100'.

A transfixion pin 1000 proceeds, as one continuous pin, through a bone and out through the skin on each of two opposed sides of an extremity. In an embodiment, the external portions of a transfixion pin 1000 are engaged with fixation hardware at both ends thereof. In an embodiment, a transfixion pin 1000 extends from one Y-frame 100, into the extremity, through a bone, out of the extremity, and into another Y-frame 100'. In contrast, in an embodiment, a fixation pin 980 (see FIGS. 7 and 8) enters the extremity only once and extends into a bone but does not exit the extremity. In an embodiment, a fixation pin 980 is supported by hardware only at one of its ends.

Figure 25:
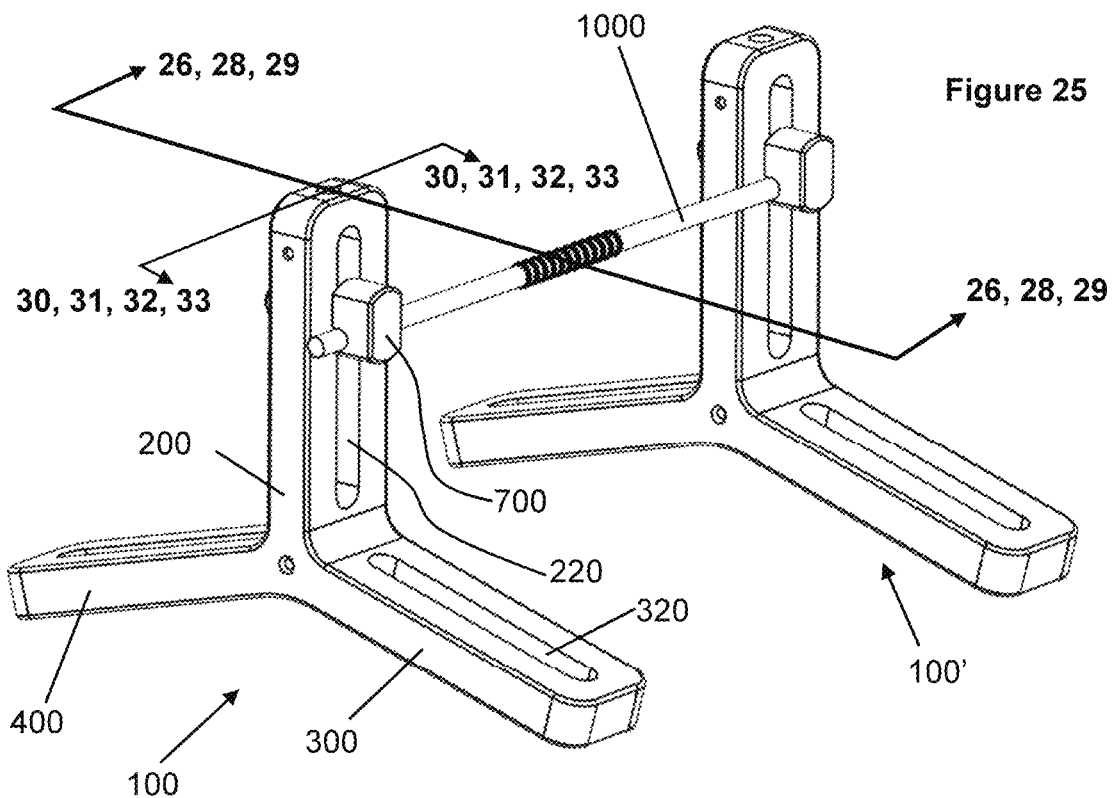
FIG. 25 is a top perspective view of a pair of Y-frames according to an embodiment of the invention, as connected by a superior transfixion pin.
Figure 26:
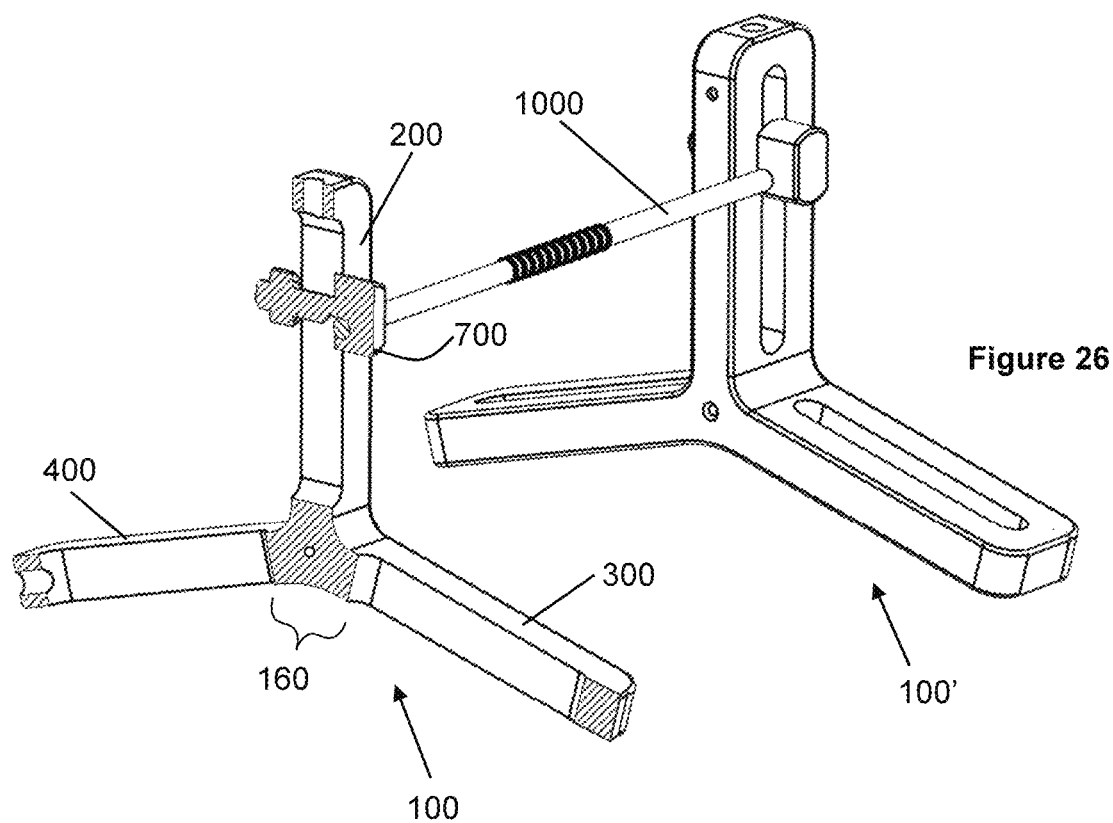
FIG. 26 is a sectional view of FIG. 25.
Figure 27:
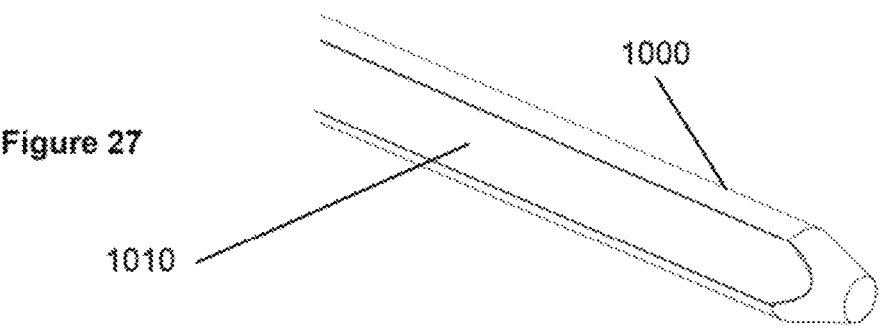
FIG. 27 shows a transfixion pin that has a flat on it.
Figure 28:
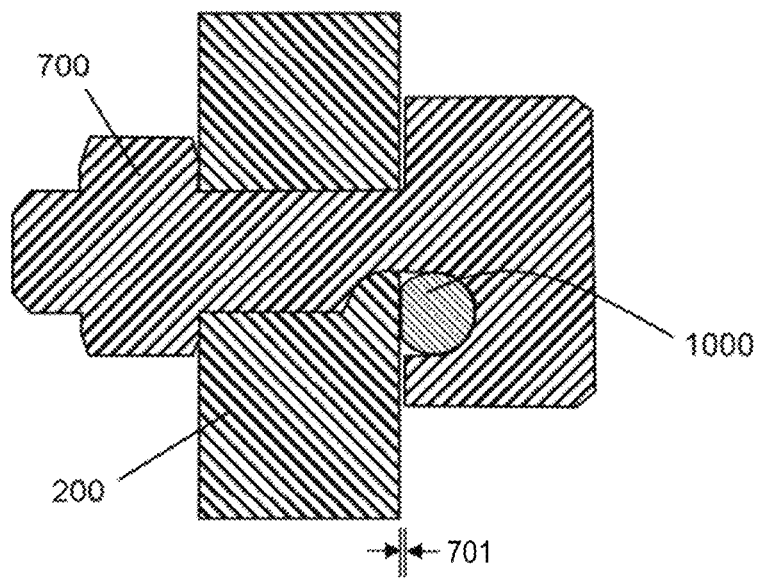
FIG. 28 shows the transfixion pin of FIG. 27 used in a configuration such that it applies a rotational constraint.
Figure 29:
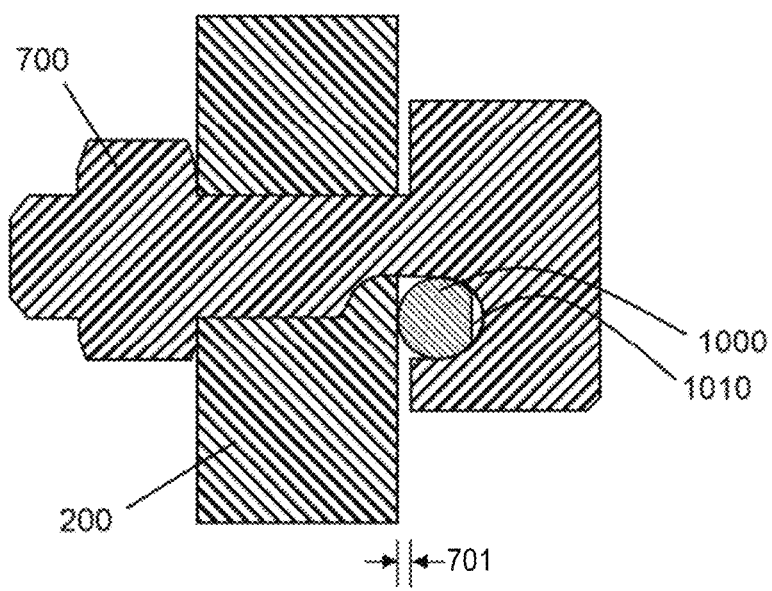
FIG. 29 shows the transfixion pin of FIG. 27 used in a configuration such that it does not apply a rotational constraint.

In an embodiment, if a transfixion pin 1000 is axisymmetric at both of its gripping ends, it can permit a range of angular orientations of the two Y-frames 100, 100' relative to each other around the longitudinal axis of the transfixion pin 1000. Such a transfixion pin 1000 is illustrated in FIG. 25 and in FIG. 26, which is a section of FIG. 25. On the other hand, as illustrated in FIGS. 27-29, if a transfixion pin 1000 is non-axisymmetric at both of its gripping ends, it can serve to define the relative angular orientation of the two Y-frames 100, 100' around the longitudinal axis of the transfixion pin 1000. In FIG. 27, it is illustrated that the transfixion pin 1000 can have a flat 1010 at one end, and in an embodiment transfixion pin 1000 can have another flat 1010 at the other end, with the two flats being coplanar with each other.

In an embodiment, during use, a transfixion pin 1000 having such flats 1010 could be used in either of two ways. If the transfixion pin 1000 is mounted as illustrated in FIG. 28 such that its flat 1010 abuts against a flat surface of an arm such as superior arm 200, then transfixion pin 1000 can impose an angular constraint defining a relative orientation of the two Y-frames 100. Alternatively, in an embodiment, the same transfixion pin 1000 could be installed as illustrated in FIG. 29 such that its round surface bears against the flat surface of the arm such as superior arm 200, In such a situation, there would not be any constraint imposed on the relative orientation of one Y-frame 100 and the other Y-frame 100' with respect to rotation around the longitudinal axis of transfixion pin 1000.

Figure 30:
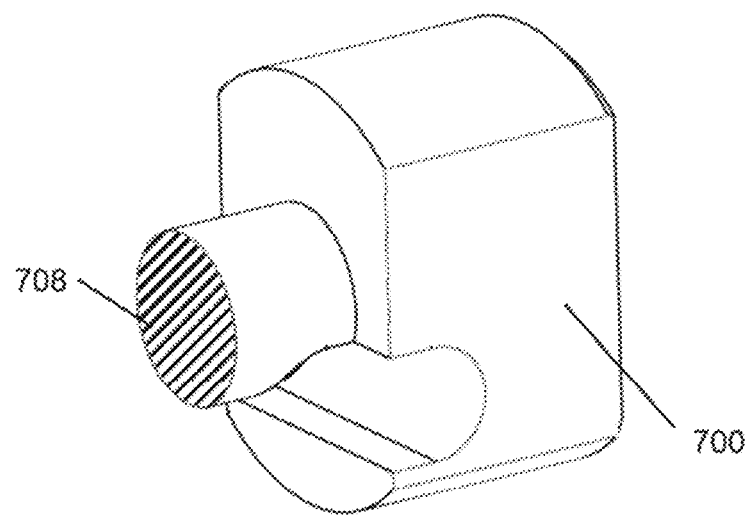
FIG. 30 shows a clamping bolt that does not apply a constraint on a certain degree of freedom of rotation.
Figure 31:
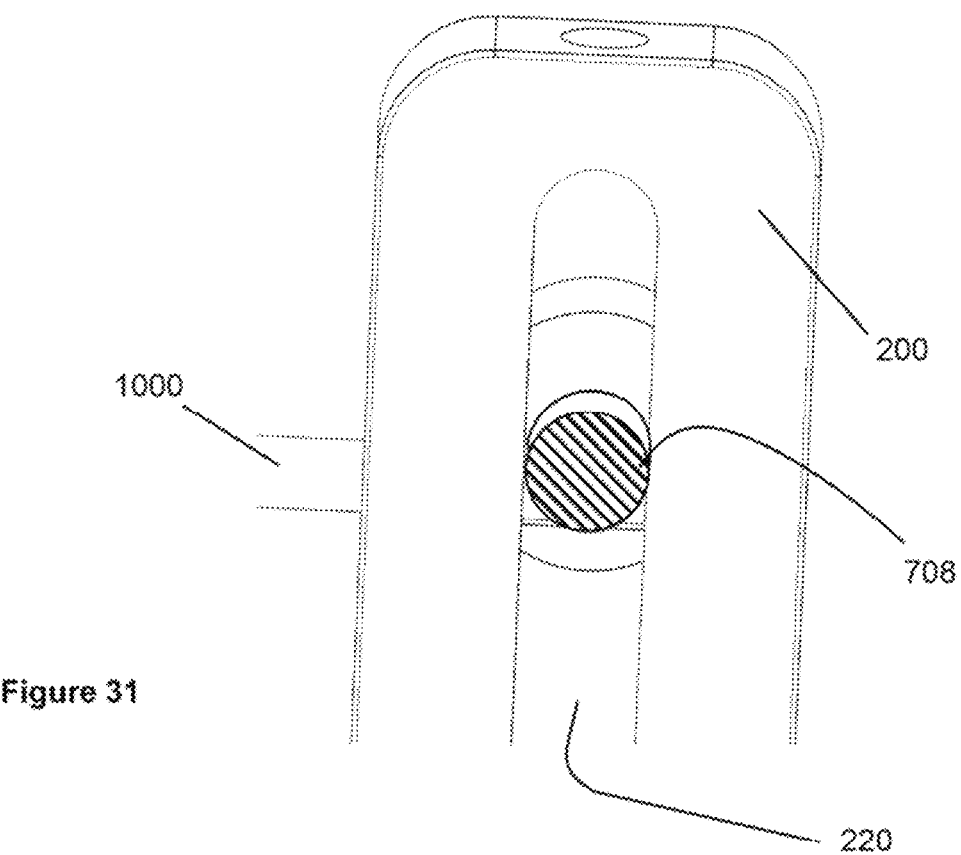
FIG. 31 shows the clamping bolt of FIG. 30 in its interaction with the superior arm slot in the superior arm.

Another type of geometric constraint is illustrated in FIGS. 30-33 for an embodiment. FIG. 30 shows a clamping bolt 700 such that the shaft 708 of the clamping bolt 700, where the clamping bolt 700 passes through slot 320, is round. FIG. 31 shows that the roundness of the shaft 708 of the clamping bolt 700 allows rotation of Y-frame 100 around the axis of the shaft 708 of clamping bolt 700, such that the overall plane of one Y-frame 100 and the overall plane of the other Y-frame 100' can be either parallel to each other or non-parallel, whichever is desired.

Figure 32:
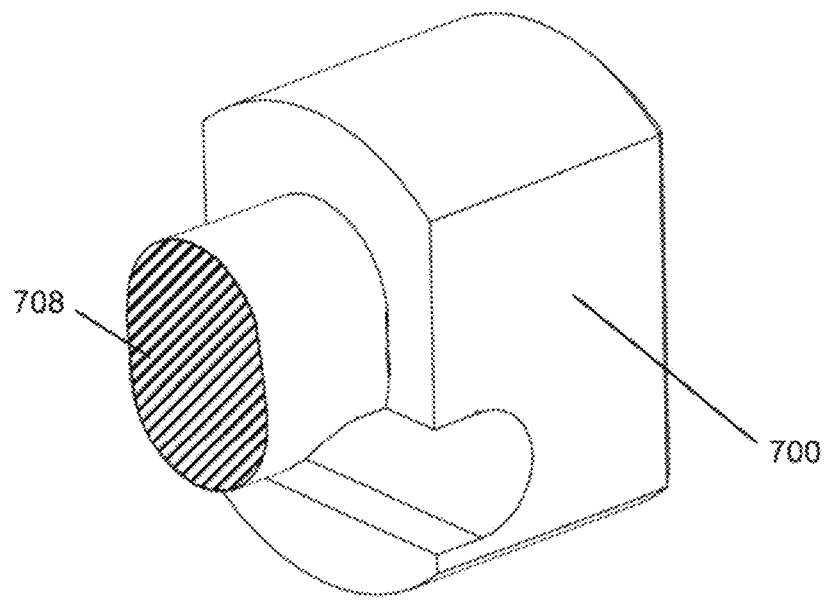
FIG. 32 shows a clamping bolt that is able to apply a constraint on a certain degree of freedom of rotation.
Figure 33:
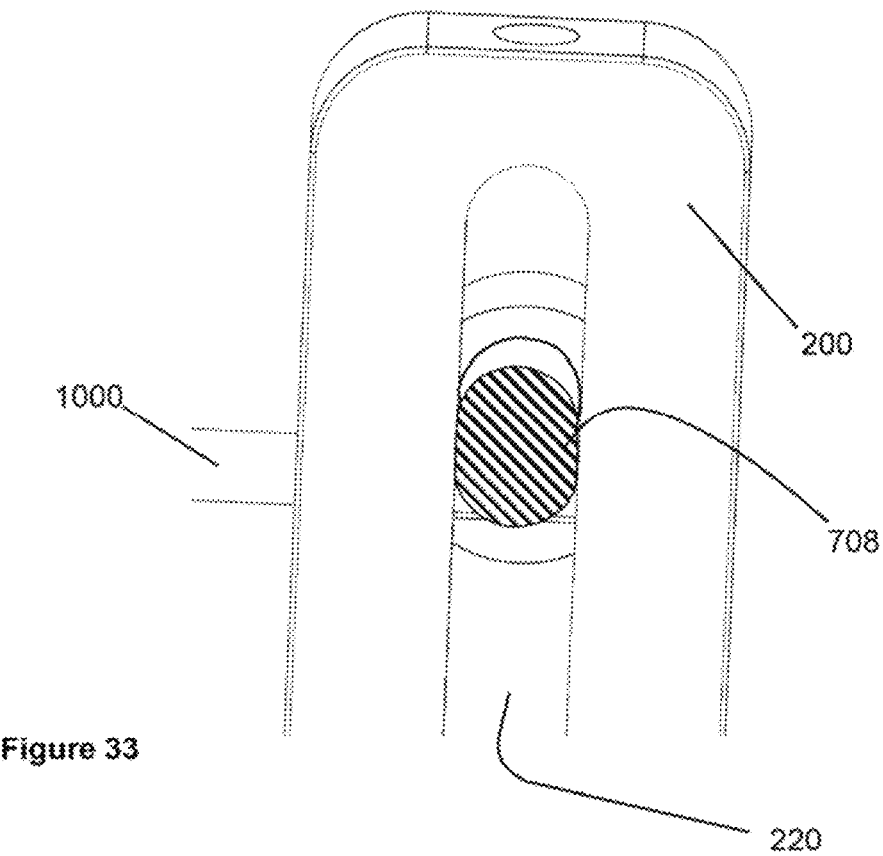
FIG. 33 shows the clamping bolt of FIG. 32 in its interaction with the superior arm slot in the superior arm.

In an embodiment, it is also possible that this interaction can be designed such as to constrain that the plane of one Y-frame 100 and the plane of the other Y-frame 100' be parallel to each other. For example, this interaction can be such that the shaft 708 of a clamping bolt 700 can have a geometric relationship with the slot 220 such that the clamping bolt 700 is prevented from rotating about the lengthwise axis of shaft 708 within the slot 220. FIG. 32 shows a clamping bolt 700 such that the shaft 708 of the clamping bolt 700 is racetrack-shaped in cross-section. FIG. 33 shows that the racetrack-shaped shaft 708 of clamping bolt 700 has external flat-to-flat dimensions that are close-fitting with the dimensions of internal surface or edges of slot 220 and therefore shaft 708 interacts with the internal surface or edges of slot 220 so as to create the constraint. A racetrack-shaped cross-section is considered to be a shape that has two parallel sides in combination with semicircles at each end. In other embodiments, there are provided other similar cross-sectional shapes, such as rounded-rectangle, or an oval or elliptical shape or still other elongated shapes. A cross-sectional shape that has some straight sides, and is closely-fitting with slot 220, might provide more effective constraint than a cross-sectional shape lacking such straight sides. In such embodiments, the non-illustrated end of shaft 708 that accepts nut 710 could be designed similarly to what is illustrated in FIGS. 25-31.

Other design features are also possible to constrain the clamping bolt 700 so as to prevent it from rotating about its own lengthwise axis within the slot 320. For example, the clamping bolt 700 could have a feature that interacts with an external feature of an arm such as arm 200, or could have a feature that interacts with yet some other feature of an arm such as arm 200.

Kit

A kit according to an embodiment of the invention, contains a solid Y-frame 100, or some form of Y-frames not disassemblable by the user, together with fixation hardware. Various embodiments of the kit comprise at least some, or all, of the following items:

Two or more Y-frames 100, 100'
Pin-holding assembly 500 (various assemblies or various rocker nuts 530)
Various shim washers 570 (thicknesses, surface shape)
Various bolts 510
Clamping bolt 700 (various)
Fixation pins 980
Transfixion pins 1000 (both round and flatted varieties)

In such a kit, if one wants to change the continuous/discrete rotational angle properties regarding orientation of a pin, one could substitute the appropriate rocker nut 530 in a pin-holding assembly 500. Alternatively, one could substitute an entire pin-holding assembly 500. If one wants to change the continuous/discrete translational properties, assuming that the arms have appropriate features, one can reorient or substitute shim washer 570. One could change a constraint of relative orientation of two Y-frames by choice of clamp bolt 700. One could change a constraint of relative orientation of two Y-frames by choice of or orientation of transfixion pin 1000.

In another embodiment of the kit, the Y-frames are themselves assemblable by the user from sub-components, which can be assembled by the user into Y-frames as desired. Various embodiments of the kit comprise at least some, or all, of the following:

At least two hubs 800, having various groove combinations (hubs may be generally cylindrical exterior or generally spherical exterior)
At least three arms for each of at least two Y-frames; arms may have various designs of groove-complementary features Bolts for assembling hubs and arms
Shim washers 570 of identical or assorted different thicknesses
Pin-holding assemblies 500 (various)

In an embodiment, a kit of this type could contain various hubs 800 having different directions of grooves or combinations of directions of grooves 830A, 830B. In an embodiment, there are provided arms 200, 300, 400 that have various types of hub-facing surfaces such as grooved in a single direction, grooved in multiple directions, or ungrooved. Each of these would define different degrees of engagement with the hub 800.

In an embodiment, for example, a hub 800 having a spherical exterior with grooves 830A, 830B in two mutually perpendicular orientations, depending on what geometry of hub-facing surface engages with it, could permit discrete angulation in one plane (if the hub-facing surface has groove-complementary features along one direction) with no arm twisting allowed; or it could permit continuous angulation in one plane (if the hub-facing surface has groove-complementary features along the other direction) with no arm twisting allowed, or it could provide continuous angulation in one plane (if the hub-facing surface is smooth) combined with arm twisting being allowed.

In an embodiment, arms 200, 300, 400 can be provided with groove-complementary features 840A, 840B that extend in one direction, or extend in two generally perpendicular directions, or arms can be provided with smooth hub-facing surfaces that do not engage grooves 830A, 830B in the hub 800 at all.

In yet another embodiment, in which the arms 200, 300, 400 can be chosen and assembled by the user, multiple versions of arms 200, 300, 400 can be provided so that the user can choose which arms he or she wishes to combine to assemble the Y-frame 100.

Methods of Use

Embodiments of the invention can also comprise a method of use of the described apparatus.

In an embodiment, during use, a transfixion pin 1000 having such flats 1010 could be used in either of two ways. If the transfixion pin 1000 is mounted as illustrated in FIG. 28 such that its flat 1010 abuts against a flat surface of an arm such as superior arm 200, then transfixion pin 1000 can impose an angular constraint defining a relative orientation of the two Y-frames 100. The gap between superior arm 200 and clamp bolt 700 is indicated at 701. Alternatively, in an embodiment, the same transfixion pin 1000 could be installed as illustrated in FIG. 29 such that its round surface bears against the flat surface of the arm such as superior arm 200. In such a situation, there would not be any constraint imposed on the relative orientation of one Y-frame 100 and the other Y-frame 100' with respect to rotation around the longitudinal axis of transfixion pin 1000. In this situation, gap 701 is somewhat wider than when there is a constraint.

Another type of geometric constraint is illustrated in FIGS. 30-33 for an embodiment. FIG. 30 shows a clamping bolt 700 such that the shaft 708 of the clamping bolt 700, where the clamping bolt 700 passes through slot 320, is round. FIG. 31, depicting a situation where constraint is not applied, shows that the roundness of the shaft 708 of the clamping bolt 700 allows rotation of Y-frame 100 around the axis of the shaft 708 of clamping bolt 700, such that the overall plane of one Y-frame 100 and the overall plane of the other Y-frame 100' can be either parallel to each other or non-parallel, whichever is desired.

In an embodiment, it is also possible that this interaction can be designed such as to constrain that the plane of one Y-frame 100 and the plane of the other Y-frame 100' be parallel to each other. For example, this interaction can be such that the shaft 708 of a clamping bolt 700 can have a geometric relationship with the slot 220 such that the clamping bolt 700 is prevented from rotating about the lengthwise axis of shaft 708 within the slot 220. FIG. 32 shows a clamping bolt 700 such that the shaft 708 of the clamping bolt 700 is racetrack-shaped in cross-section. FIG. 33, depicting a case where constraint is applied, shows that the racetrack-shaped shaft 708 of clamping bolt 700 has external flat-to-flat dimensions that are close-fitting with the dimensions of internal surface or edges of slot 220 and therefore shaft 708 interacts with the internal surface or edges of slot 220 so as to create the constraint. A racetrack-shaped cross-section is considered to be a shape that has two parallel sides in combination with semicircles at each end. In other embodiments, there are provided other similar cross-sectional shapes, such as rounded-rectangle, or an oval or elliptical shape or still other elongated shapes. A cross-sectional shape that has some straight sides, and is closely-fitting with slot 220, might provide more effective constraint than a cross-sectional shape lacking such straight sides. In such embodiments, the non-illustrated end of shaft 708 that accepts nut 710 could be designed similarly to what is illustrated in FIGS. 25-31.

In an embodiment, if apparatus includes provision for arm-twisting rotational adjustment or for angulation of arms relative to each other, adjustment of either of these geometric variables could be made at the time of use.

In an embodiment, if components are provided in the form of a hub 800 (or multiple hubs) and arms that are connectable to the hub 800, choices could be made at the time of use as to which arms are connected to a hub 800, and in what orientation.

In an embodiment, if the apparatus includes a transfixion pin 1000 that contains flats 1010 on it, the transfixion pin 1000 could be used in either a constraining or a non-constraining mode depending on the rotational position of the transfixion pin 1000 around the longitudinal axis of the transfixion pin 1000. This decision can be made at the time of use.

In an embodiment, as described herein, it is possible that a one clamping bolt 700 could be provided for use in a constraining mode and another clamping bolt 700 could be provided for use in a non-constraining mode. The choice could be made at the time of use. In an embodiment it could also be possible, depending on the design of the clamping bolt 700 and associated features of the arms 200, 300, 400, to use a single clamping bolt 700 in either mode depending on how the clamping bolt 700 is installed such as with respect to angle around the longitudinal axis of the shaft 708 of the clamping bolt 700.

Further Embodiments and Modifications

As illustrated herein, where two Y-frames 100, 100' are shown, the Y-frames 100, 100' on opposite sides of the foot are shown as being identical to each other (see FIG. 23). However, if desired, in alternate embodiments, the Y-frames 100, 100' could differ from each other in any one or more of dimensions or features described herein, or in other dimensions or features.

Although illustrations herein show the clamping bolt 700 on the superior arm 200 and the pin-holding assembly 500 on the anterior arm 300 and posterior arm 400, it is possible for the clamping bolt 700 to be used on any arm 200, 300, 400. Similarly, the pin-holding assembly 500 could be used on any arm 200, 300, 400. In illustrations, a transfixion pin 1000 is shown being grasped by a clamping bolt 700 and fixation pins 980 are shown being grasped by a pin-holding assembly 500. However, it is to be understood that either a transfixion pin 1000 or a fixation pin 980 can be grasped by either a clamping bolt 700 or a pin-holding assembly 500. Transfixion pins 1000 could be used on any arm 200, 300, 400, and fixation pins 980 could be used on any arm 200, 300, 400, in any combination and in any quantity.

In illustrations, arm-twisting rotational joints 496 are shown on one arm 400, but it can be understood that such arm-twisting rotational joints 496 may be provided on whatever arms may be desired.

In illustrations of the pin-holding assembly 500, it is shown that the bolt 510 both attaches the pin-holding assembly 500 to the arm and tightens the clamp 550 around the pin. In an embodiment, it would be possible to design the pin-holding assembly 500 such that one bolt 510 anchors the pin-holding assembly 500 to the arm and a different bolt causes tightening of the clamp around the pin.

In an embodiment, there can be provided additional features on the Y-frames 100, 100', such as for interfacing with still other mechanical components for fixation or for other purposes.

In an embodiment, the arms 200, 300, 400 of the Y-frames 100, 100' are marked with dimensional scales or other indicators that may be useful for clinical purposes.

The described apparatus is shown for use on a human foot, but it should be understood that the described apparatus could also be used on other parts of the body.

In general, any combination of disclosed features, components and methods described herein is possible. Steps of a method can be performed in any order that is physically possible.

All cited references are incorporated by reference herein.

Although embodiments have been disclosed, it is not desired to be limited thereby. Rather, the scope should be determined only by the appended claims.

What is claimed is:

1. An apparatus for fixating at least one bone, said apparatus comprising:
   a frame comprising a superior arm, an anterior arm and a posterior arm, said superior arm, anterior arm and posterior arm extending outwardly in respective different directions from a central region,
   said superior arm having a superior arm axis extending generally along a lengthwise direction of said superior arm through said central region, said superior arm having therethrough a superior arm slot extending generally along at least a portion of a length of said superior arm and being generally aligned with said superior arm axis,
   said anterior arm having an anterior arm axis extending generally along a lengthwise direction of said anterior arm through said central region, said anterior arm having therethrough an anterior arm slot extending generally along at least a portion of a length of said anterior arm and being generally aligned with said anterior arm axis,
   said posterior arm having a posterior arm axis extending generally along a lengthwise direction of said posterior arm through said central region, said posterior arm having therethrough a posterior arm slot extending generally along at least a portion of a length of said posterior arm and being generally aligned with said posterior arm axis, wherein none of said superior arm axis, said anterior arm axis and said posterior arm axis are collinear with each other, and wherein each of said slots is configured to receive mounting hardware that is a) mountable on said arms through respective ones of said slots, b) able to occupy a plurality of translational positions along said slots, and c) able to hold at least one bone-fixating pin.

2. The apparatus of claim 1, wherein said superior arm slot, said anterior arm slot and said posterior arm slot define respective arm slot planes that are all substantially coplanar with each other and that extend through said superior arm slot, said anterior arm slot and said posterior arm slot, respectively.

3. The apparatus of claim 2, wherein at least one of said arms comprises a surface that is substantially flat and substantially perpendicular to its respective arm slot plane, and wherein the slot extending through said at least one arm extends through said substantially flat surface.

4. The apparatus of claim 1 further comprising mounting hardware which comprises at least one pin-holding assembly that is capable of holding a pin at a plurality of angular positions around a first axis of rotation and is capable of holding said pin at a plurality of angular positions around a second axis of rotation that is different from said first axis of rotation, neither of said axes of rotation being a longitudinal axis of said pin.

5. The apparatus of claim 1 further comprising mounting hardware which comprises at least one pin-holding assembly that is capable of holding a pin at a plurality of angular positions around a first axis of rotation, wherein each of said angular positions is only permitted to be one of a plurality of discrete angular positions.

6. The apparatus of claim 1, wherein one of said arms comprises a flat surface and wherein said apparatus further comprises mounting hardware comprising at least one clamping bolt that is capable of clamping a pin directly against said flat surface.

7. The apparatus of claim 1 further comprising mounting hardware which comprises a pin-holding assembly and a clamping bolt, wherein said pin-holding assembly provides more degrees of freedom for positioning a respective pin than does said clamping bolt.

8. The apparatus of claim 1, further comprising mounting hardware that, in a first direction of translation, allows continuous adjustment of the position of said pin, and that, in a second direction of translation different from said first direction of translation, allows adjustment in discrete steps of the position of said pin.

9. The apparatus of claim 1, further comprising mounting hardware that, in rotation about a first axis of rotation, allows continuous adjustment of the position of said pin, and in rotation about a second axis of rotation that is different from said first axis of rotation, allows adjustment in discrete steps of the position of said pin.

10. The apparatus of claim 1 further comprising mounting hardware which comprises first pin fixation hardware attachable to said arms and second pin fixation hardware attachable to said arms, wherein said first pin fixation hardware and said second pin fixation hardware have different numbers of degrees of freedom that allow adjustment in rotation, or have different numbers of degrees of freedom that allow adjustment in translation.

11. The apparatus of claim 1 further comprising mounting hardware which comprises first pin fixation hardware attachable to said arms and second pin fixation hardware attachable to said arms, wherein said first pin fixation hardware and said second pin fixation hardware have different numbers of degrees of freedom that allow continuous adjustment, or have different numbers of degrees of freedom that allow discrete adjustment.

12. The apparatus of claim 1, wherein said superior arm, said anterior arm and said posterior arm have fixed angular relationships with each other such that if said superior arm at least approximately aligns with a lower leg of a patient, said anterior arm at least approximately aligns with an anterior portion of a foot of the patient, and said posterior arm at least approximately aligns with a posterior portion of said foot of the patient.

13. The apparatus of claim 1, wherein said superior arm and said anterior arm and said posterior arm are capable of occupying a plurality of angular positions with respect to each other around a central axis hole that passes through a common intersection point within said central region, said angular positions all being within a common plane.

14. The apparatus of claim 13, further comprising a locking device, said locking device being capable of locking said superior arm, said anterior arm and said posterior arm in desired angular positions relative to each other.

15. The apparatus of claim 14, wherein at least some of said angular positions are discretely defined angular positions, and wherein said locking device further comprises detents at said discretely defined angular positions.

16. The apparatus of claim 1, wherein at least one of said superior arm and said anterior arm and said posterior arm contains a respective joint that is capable of allowing a distal portion of said at least one arm to rotate around the arm axis of said at least one arm in such a way as to be able to occupy a plurality of angular positions with respect to a central portion of said respective arm.

17. The apparatus of claim 16, wherein the slot of said at least one arm is located entirely within said distal portion of said respective arm.

18. The apparatus of claim 16, wherein said superior arm and said anterior arm and said posterior arm are capable of occupying a plurality of angular positions with respect to each other around a central axis hole that passes through a common intersection point within said central region, said angular positions all being within a common plane.

19. The apparatus of claim 16, further comprising a locking device, said locking device being capable of locking a distal portion of said arm with respect to a central portion of said at least one arm.

20. The apparatus of claim 1 wherein said superior arm axis, said anterior arm axis and said posterior arm axis intersect at a common intersection point within said central region and occupy a common plane.

21. The apparatus of claim 1 wherein said frame is integrally formed.

22. An apparatus for fixating at least one bone, said apparatus comprising:

a frame comprising a superior arm, an anterior arm and a posterior arm, said superior arm, anterior arm and posterior arm extending outwardly in respective different directions from a central region, said superior arm having a superior arm axis extending generally along a lengthwise direction of said superior arm through said central region, said superior arm having therethrough a superior arm slot extending generally along at least a portion of a length of said superior arm and being generally aligned with said superior arm axis, said anterior arm having an anterior arm axis extending generally along a lengthwise direction of said anterior arm through said central region, said anterior arm having therethrough an anterior arm slot extending generally along at least a portion of a length of said anterior arm and being generally aligned with said anterior arm axis, said posterior arm having a posterior arm axis extending generally along a lengthwise direction of said posterior arm through said central region, said posterior arm having therethrough a posterior arm slot extending generally along at least a portion of a length of said posterior arm and being generally aligned with said posterior arm axis, wherein none of said superior arm axis, said anterior arm axis and said posterior arm axis are collinear with each other, and wherein each of said slots is configured to receive mounting hardware that is a) mountable on said arms through respective ones of said slots, b) able to occupy a plurality of translational positions along said slots, and c) able to hold at least one bone-fixating pin, and wherein said mounting hardware comprises a clamp having a clamp cross-hole having internal grooves having a clamp hole angular spacing therebetween, and comprises a rocker nut having external teeth having a rocker nut angular spacing therebetween, wherein one of said clamp hole angular spacing and said rocker nut angular spacing is an integer multiple of the other.

\* \* \* \* \*